US007751057B2

(12) United States Patent
Oldenburg et al.

(10) Patent No.: US 7,751,057 B2
(45) Date of Patent: Jul. 6, 2010

(54) MAGNETOMOTIVE OPTICAL COHERENCE TOMOGRAPHY

(75) Inventors: Amy L. Oldenburg, Urbana, IL (US); Stephen A. Boppart, Champaign, IL (US); Vasilica Crecea, Urbana, IL (US); Xing Liang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 36 days.

(21) Appl. No.: 12/041,366

(22) Filed: Mar. 3, 2008

(65) Prior Publication Data
US 2009/0185166 A1 Jul. 23, 2009

Related U.S. Application Data

(60) Provisional application No. 61/022,276, filed on Jan. 18, 2008.

(51) Int. Cl.
*G01B 11/02* (2006.01)
(52) U.S. Cl. ...................................... 356/497
(58) Field of Classification Search ................. 356/479, 356/497
See application file for complete search history.

(56) References Cited

U.S. PATENT DOCUMENTS

| 4,522,811 | A | 6/1985 | Eppstein et al. |
| 4,930,516 | A | 6/1990 | Alfano et al. |
| 5,095,487 | A | 3/1992 | Meyerhofer et al. |
| 5,199,431 | A | 4/1993 | Kittrell et al. |
| 5,247,343 | A | 9/1993 | Burch |
| 5,280,788 | A | 1/1994 | Janes et al. |
| 5,303,710 | A | 4/1994 | Bashkansky et al. |
| 5,362,478 | A | 11/1994 | Desai et al. |
| 5,439,686 | A | 8/1995 | Desai et al. |
| 5,451,785 | A | 9/1995 | Faris |
| 5,459,570 | A | 10/1995 | Swanson et al. |
| 5,491,524 | A | 2/1996 | Hellmuth et al. |
| 5,498,421 | A | 3/1996 | Grinstaff et al. |

(Continued)

FOREIGN PATENT DOCUMENTS

EP      1 154 224      11/2001

(Continued)

OTHER PUBLICATIONS

Oldenburg et al, Magnetomotive contrast for in vivo optical coherence tomography, Aug. 2005 Optical Society of America, vol. 13 No. 17, Optics Express 6597.*

(Continued)

*Primary Examiner*—Tarifur Chowdhury
*Assistant Examiner*—Jonathon D. Cook
(74) *Attorney, Agent, or Firm*—Evan Law Group LLC

(57) ABSTRACT

A spectral-domain magnetomotive optical coherence tomography apparatus, includes (a) a spectral-domain optical coherence tomography device, and (b) a magnet. The magnet is coupled with the optical coherence tomography device so that changes in the magnetic field are coordinated with collection of data by the optical coherence tomography device. This device may be used to examine a sample by spectral-domain magnetomotive optical coherence tomography, which includes examining the sample with a spectral-domain optical coherence tomography device, to collect optical coherence tomography data. The sample contains magnetic particles, and the magnetic particles are subjected to a changing magnetic field during the examining.

30 Claims, 9 Drawing Sheets

U.S. PATENT DOCUMENTS

| | | |
|---|---|---|
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,648,506 A | 7/1997 | Desai et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,752,518 A | 5/1998 | McGee et al. |
| 5,836,877 A | 11/1998 | Zavislan |
| 5,891,619 A | 4/1999 | Zakim et al. |
| 5,914,806 A | 6/1999 | Gordon, II et al. |
| 5,921,926 A | 7/1999 | Rolland et al. |
| 5,930,026 A | 7/1999 | Jacobson et al. |
| 5,972,493 A | 10/1999 | Iwasaki et al. |
| 5,994,690 A | 11/1999 | Kulkarni et al. |
| 5,995,645 A | 11/1999 | Soenksen et al. |
| 6,002,476 A | 12/1999 | Treado |
| 6,002,480 A | 12/1999 | Izatt et al. |
| 6,037,579 A | 3/2000 | Chan et al. |
| 6,068,600 A | 5/2000 | Johnson et al. |
| 6,069,932 A | 5/2000 | Peshkin et al. |
| 6,091,496 A | 7/2000 | Hill |
| 6,108,081 A | 8/2000 | Holtom et al. |
| 6,111,645 A | 8/2000 | Tearney et al. |
| 6,134,003 A | 10/2000 | Teamey et al. |
| 6,151,522 A | 11/2000 | Alfano et al. |
| 6,156,292 A | 12/2000 | Quay |
| 6,159,445 A | 12/2000 | Klaveness et al. |
| 6,167,297 A | 12/2000 | Benaron |
| 6,208,886 B1 | 3/2001 | Alfano et al. |
| 6,219,137 B1 | 4/2001 | Vo-Dinh |
| 6,231,834 B1 | 5/2001 | Unger et al. |
| 6,246,892 B1 | 6/2001 | Chance |
| 6,246,901 B1 | 6/2001 | Benaron |
| 6,249,271 B1 | 6/2001 | Albert et al. |
| 6,262,706 B1 | 7/2001 | Albert et al. |
| 6,262,833 B1 | 7/2001 | Loxley et al. |
| 6,264,917 B1 | 7/2001 | Klaveness et al. |
| 6,264,918 B1 | 7/2001 | Johnson et al. |
| 6,280,704 B1 | 8/2001 | Schutt et al. |
| 6,300,932 B1 | 10/2001 | Albert |
| 6,307,633 B1 | 10/2001 | Mandella et al. |
| 6,307,634 B2 | 10/2001 | Hitzenberger et al. |
| 6,312,304 B1 | 11/2001 | Duthaler et al. |
| 6,315,981 B1 | 11/2001 | Unger |
| 6,344,272 B1 | 2/2002 | Oldenburg et al. |
| 6,363,163 B1 | 3/2002 | Xu et al. |
| 6,428,811 B1 | 8/2002 | West et al. |
| 6,485,413 B1 | 11/2002 | Boppart et al. |
| 6,514,767 B1 | 2/2003 | Natan |
| 6,529,277 B1 | 3/2003 | Weitekamp |
| 6,530,944 B2 | 3/2003 | West et al. |
| 6,538,805 B1 | 3/2003 | Norwood et al. |
| 6,539,156 B1 | 3/2003 | Dickson et al. |
| 6,560,478 B1 | 5/2003 | Alfano et al. |
| 6,564,087 B1 | 5/2003 | Pitris et al. |
| 6,574,401 B2 | 6/2003 | Neuberger et al. |
| 6,584,335 B1 | 6/2003 | Haar et al. |
| 6,615,063 B1 | 9/2003 | Ntziachristos et al. |
| 6,618,423 B1 | 9/2003 | Dekorsy et al. |
| 6,689,067 B2 | 2/2004 | Sauer et al. |
| 6,690,966 B1 | 2/2004 | Rava et al. |
| 6,795,777 B1 | 9/2004 | Scully et al. |
| 6,825,928 B2 | 11/2004 | Liu et al. |
| 6,839,586 B2 | 1/2005 | Webb |
| 6,922,583 B1 | 7/2005 | Perelman et al. |
| 7,181,266 B2 | 2/2007 | Frangioni et al. |
| 7,198,777 B2* | 4/2007 | Boppart et al. ............. 424/9.6 |
| 7,217,410 B2 | 5/2007 | Suslick et al. |
| 7,610,074 B2 | 10/2009 | Boppart et al. |
| 2002/0028993 A1 | 3/2002 | Hainfeld |
| 2002/0054912 A1 | 5/2002 | Kim et al. |
| 2002/0087071 A1 | 7/2002 | Schmitz et al. |
| 2002/0168161 A1 | 11/2002 | Price et al. |
| 2003/0045798 A1 | 3/2003 | Hular et al. |
| 2003/0068496 A1 | 4/2003 | Wei et al. |
| 2003/0082104 A1 | 5/2003 | Mertelmeier |
| 2003/0171678 A1 | 9/2003 | Batten et al. |
| 2004/0015062 A1 | 1/2004 | Ntziachristos et al. |
| 2004/0023415 A1 | 2/2004 | Sokolov et al. |
| 2004/0024307 A1 | 2/2004 | Golman et al. |
| 2004/0058458 A1 | 3/2004 | Anker et al. |
| 2004/0186359 A1 | 9/2004 | Beaudoin et al. |
| 2004/0249268 A1 | 12/2004 | Da Silva |
| 2005/0004453 A1 | 1/2005 | Tearney et al. |
| 2005/0036150 A1 | 2/2005 | Izatt et al. |
| 2005/0078363 A1 | 4/2005 | Gugel |
| 2005/0149002 A1 | 7/2005 | Wang et al. |
| 2005/0168735 A1 | 8/2005 | Boppart et al. |
| 2005/0171433 A1* | 8/2005 | Boppart et al. ............. 600/473 |
| 2006/0039004 A1* | 2/2006 | de Boer et al. ............. 356/479 |
| 2006/0066848 A1 | 3/2006 | Frankel |
| 2006/0109478 A1* | 5/2006 | Tearney et al. ............. 356/479 |
| 2006/0192969 A1 | 8/2006 | Marks et al. |
| 2006/0281068 A1 | 12/2006 | Maier et al. |
| 2006/0285635 A1 | 12/2006 | Boppart et al. |
| 2006/0292839 A1 | 12/2006 | Yi et al. |
| 2007/0203404 A1 | 8/2007 | Zysk et al. |
| 2008/0140341 A1 | 6/2008 | Ralston et al. |
| 2008/0281205 A1 | 11/2008 | Naghavi et al. |
| 2009/0185166 A1 | 7/2009 | Oldenburg et al. |
| 2009/0185191 A1 | 7/2009 | Boppart et al. |
| 2009/0221920 A1 | 9/2009 | Boppart et al. |

FOREIGN PATENT DOCUMENTS

| | | |
|---|---|---|
| EP | 1 312 912 | 5/2003 |
| EP | 1 447 043 | 8/2004 |
| EP | 0 963 540 | 3/2006 |
| WO | WO 90/01697 | 2/1990 |
| WO | WO 97/32182 | 9/1997 |
| WO | WO98/30873 | 7/1998 |
| WO | WO 98/38907 | 9/1998 |
| WO | WO99/06794 | 2/1999 |
| WO | WO99/58972 | 11/1999 |
| WO | WO 00/42906 | 7/2000 |
| WO | WO 00/42912 | 7/2000 |
| WO | WO02/41760 | 5/2002 |
| WO | WO 02/088705 | 11/2002 |
| WO | WO03/061454 | 7/2003 |
| WO | WO2005/028663 | 3/2005 |
| WO | WO2006/020302 | 2/2006 |
| WO | WO2006/032009 | 3/2006 |
| WO | WO2006/099191 | 9/2006 |
| WO | WO2006/135628 | 12/2006 |
| WO | WO 2007/027194 | 3/2007 |
| WO | WO 2007/090147 | 9/2007 |
| WO | WO 2008/008774 | 1/2008 |

OTHER PUBLICATIONS

Ai et al., "Electrostatic layer-by-layer nanoassembly on biological microtemplates: platelets", Biomacromolecules, 3:560-564, 2002.

Amsden et al., "An examination of factors affecting the size, distribution, and release characteristics of polymer microbeads made using electrostatics", J. Control. Release, 43:183-196, 1997.

Amsden, "The production of uniformly sized polymer microspheres", Pharm. Res., 16:1140-1143, 1999.

Balasubramanian et al., "Extraction and dispersion of large gold nanoparticles in nonpolar solvents", J. Dispers. Sci. Tech. 22:485-89, 2001.

Balasubramanian et al., "Dispersion and stability studies of resorcinarene-encapsulated gold nanoparticles", Langmuir, 18:3676-81, 2002.

Barton et al., "Use of microbubbles as an optical coherence tomography contrast agent", Acad. Radiol, 9, (Suppl 1):552-555, 2002.

Blackwell et al., "New approaches to olefin cross-metathesis", J. Am. Chem. Soc., 122:58-71, 2000.

Boppart et al., "Imaging Developing Neural Morphology Using Optical Coherence Tomography", J. Neuroscience Methods, vol. 70, pp. 65-72, 1996.

Boppart et al., "Investigation of Developing Embryonic Morphology Using Optical Coherence Tomography", Developmental Biology, vol. 177, pp. 54-63, 1996.

Boppart et al., "Noninvasive assessment of the developing Xenopus cardiovascular system using optical coherence tomography", Proc. Natl. Acad. Sci. USA, 94: 4256-4261, 1997.

Boppart et al., "Forward-Imaging Instruments for Optical Coherence Tomography", Optics Letters, vol. 22, No. 21, pp. 1618-1620, 1997.

Boppart et al., "In vivo Cellular Optical Coherence Tomography Imaging", Nature Medicine, vol. 4, No. 7, pp. 861-865, 1998.

Boppart et al., "Intraoperative Assessment of Microsurgery with Three-Dimensional Optical Coherence Tomography", Radiology, vol. 208, pp. 81-86, 1998.

Boppart et al., "Optical Coherence Tomography for Neurosurgical Imaging of Human Intracortical Melanoma", Neurosurgery, vol. 43, No. 4, pp. 834-841, 1998.

Boppart, "Surgical Diagnostics, Guidance, and Intervention Using Optical Coherence Tomography", Ph.D. Thesis, Massachusetts Institute of Technology, Cambridge, MA, 226 pages, 1998.

Boppart et al., "High-Resolution Optical Coherence Tomography-Guided Laser Ablation of Surgical Tissue", J. Surgical Research, 82:275-84, 1999.

Boppart, "Endoscopic Optical Coherence Tomography Imaging of Barrett's Esophagus", M.D. Thesis, Harvard University, 2000.

Bouma et al., "High resolution optical coherence tomographic imaging using a mode-locked Ti:Al$_2$O$_3$ laser source", Optics Letter, 20:1486-1488, 1995.

Bouma et al., "High-resolution imaging of the human esophagus and stomach in vivo using optical coherence tomography", Gastrointestinal Endoscopy, 51: 467-474, 2000.

Boyer et al., "Photothermal Imaging of Nanometer-Sized Metal Particles Among Scatterers", Science, 297:1160-63, 2002.

Brezinski et al., "Optical Coherence Tomography for Optical Biopsy: Properties and Demonstration of Vascular Pathology", Circulation, vol. 93, pp. 1206-1213, 1996.

Bugaj et al., "Novel fluorescent contrast agents for optical imaging of in vivo tumors based on a receptor-targeted dye-peptide conjugate platform", J. Biomedical Optics, 6:122-33, 2001.

Burns et al., "Tumor-localizing and photosensitizing properties of hematoporphyrin derivative in hamster buccal pouch carcinoma", Oral Surg. Oral Med. Oral Pathol., 61:368-372, 1986.

Cain et al., "Thresholds for Visible Lesions in the Primate Eye Produced by Ultrashort Near-Infrared Laser Pulses", Investigative Ophthalmology & Visual Science, 40:2343-49, 1999.

Cain et al., "Visible Retinal Lesions from Ultrashort Laser Pulses in the Primate Eye", Investigative Ophthalmology & Visual Science, 36:879-888, 1995.

Caruso et al., "Nanoengineering of inorganic and hybrid hollow spheres by colloidal templating", Science, 282:1111-1114, 1998.

Cepak et al., "Preparation and Stability of Template-Synthesized Metal Nanorod Sols in Organic Solvents", J. Phys. Chem. B, 102:9985-90, 1998.

Chen et al., "Noninvasive Imaging of In Vivo Blood Flow Velocity Using Optical Doppler Tomography", Optics Letters, vol. 22, pp. 1119-1121, 1997.

Christiansen et al., "Physical and biochemical characterization of Albunex™, a new ultrasound contrast agent consisting of air-filled albumin microparticles suspended in a solution of human albumin", Biotechnol. Appl. Biochem., 19:307-20, 1994.

Clark et al., "Second harmonic generation properties of fluorescent polymer-encapsulated gold nanoparticles", J. Am. Chem. Soc., 122:10234-35, 2000.

de Boer et al., "Two-Dimensional Birefringence Imaging in Biological Tissue by Polarization-Sensitive Optical Coherence Tomography", Optics Letters, vol. 22, pp. 934-936, 1997.

Decher "Fuzzy Nanoassemblies: Toward Layered Polymeric Multicomposites", Science, 277:1232-1237, 1997.

Desai et al., "Controlled and targeted drug delivery with biocompatible protein shell microspheres", 20th Annual Meeting of Society of Biomaterials, Apr. 4-9, 1994, Boston, MA: Proc. Soc. Biomaterial, 20:112, 1994.

Dick et al., "Computed tomography of experimental liver abscesses using a new liposomal contrast agent", Investigative Radiology, 31:194-203, 1996.

Dowlatshahi et al., "Histologic Evaluation of Rat Mammary Tumor Necrosis by Interstitial Nd:YAG Laser Hyperthermia", Lasers in Surgery and Medicine, 12:159-164, 1992.

Drexler et al., "In vivo Ultrahigh-Resolution Optical Coherence Tomography", Optics Letters, vol. 24, No. 17, pp. 1221-1223, 1999.

El-Sayed "Some interesting properties of metals confined in time and nanometer space of different shapes", Accounts of Chemical Research, 34:257-64, 2001.

Freeman et al., "Self-Assembled Metal Colloid Monolayers: An Approach to SERS Substrates", Science, 267:1629-1632, 1995.

Fu et al., "Visual evidence of acidic environment within degrading poly(lactic-co-glycolic acid) (PLGA) microspheres", Pharmaceutical Research, 17:100-106, 2000.

Fujimoto et al., "Optical biopsy and imaging using optical coherence tomography", Nature Medicine, 1:970-972, 1995.

Gazelle et al., "Nanoparticulate computed tomography contrast agents for blood pool and liver-spleen imaging", Acad. Radiol., 1:373-376, 1994.

Geny et al., "Safety of a new transpulmonary echocontrast agent (Albunex®) in repeated echocardiographic studies in patients", Clin. Cardiol., 20:111-115, 1997.

Gimenez-Conti et al., "The hamster cheek pouch carcinogenesis model", J. Cellular Biochemistry Supplement, 17F:83-90, 1993.

Gram, "Drug absorption and distribution", in Modern Pharmacology with Clinical Applications 5$^{th}$ Ed., Craig et al., eds., Little, Brown, & Co., Inc.; Boston, MA, pp. 13-24, 1997.

Grinstaff et al., "Air-filled proteinaceous microbubbles: synthesis of an echo-contrast agent", Proc. Natl. Acad. Sci. USA, 88:7708-7710, 1991.

Grubbs et al., "Ring-Closing Metathesis and Related Processes in Organic Synthesis", Acc. Chem. Res., 28:446-52, 1995.

Haes et al., "A nanoscale optical biosensor: sensitivity and selectivity of an approach based on the localized surface plasmon resonance spectroscopy of triangular silver nanoparticles", J. Am. Chem. Soc., 124:10596-604, 2002.

Handley et al., "Colloidal gold labeling studies related to vascular and endothelial function, hemostasis and receptor-mediated processing of plasma macromolecules", European J. Cell Biology, 43:163-74, 1987.

Handley et al., "Colloidal gold-low density lipoprotein conjugates as membrane receptor probes", Proc. Natl. Acad. Sci. USA, 78:368-71, 1981.

Handley "Methods for Synthesis of Colloidal Gold", Colloidal Gold: Principles, Methods, and Applications, (Academic Press), vol. 1, pp. 13-32, 1989.

Hardikar et al., "Coating of nanosize silver particles with silica", J. Colloid and Interface Science, 221:133-36, 2000.

Harrington et al., "Gene therapy for prostate cancer: current status and future prospects", J. Urology, 166:1220-33, 2001.

Hartl et al., "Ultrahigh-Resolution Optical Coherence Tomography Using Continuum Generation in an Air-Silica Microstructure Optical Fiber", Optics Letters, 26:608-610, 2001.

Hee et al., "Optical coherence tomography of the human retina", Arch. Ophthalmol. 113: 325-332, 1995.

Hiergeist et al., "Application of magnetite ferrofluids for hyperthermia", J. Magnetism and Magnetic Materials, 201:420-22, 1999.

Hirsch et al., "A Whole Blood Immunoassay Using Gold Nanoshells", Analytical Chemistry, 75:2377-2381, 2003.

Huang et al., "Optical Coherence Tomography", Science, 254: 1178-1181, 1991.

Jackson et al., "Silver Nanoshells:Variations in Morphologies and Optical Properties", J. Phys. Chem. B, 105:2743-46, 2001.

Jana et al., "Wet chemical synthesis of high aspect ratio cylindrical gold nanorods", J. Phys. Chem. B, 105:4065-67, 2001.

Jang et al., "Visualization of Coronary Atherosclerotic Plaques in Patients Using Optical Coherence Tomography: Comparison With Intravascular Ultrasound", J. American College of Cardiology, 39:604-609, 2002.

Jensen et al., "Electrodynamics of noble metal nanoparticles and nanoparticle clusters", J. Cluster Science, 10:295-317, 1999.

Jin et al., "Photoinduced conversion of silver nanospheres to nanoprisms", Science, 294:1901-03, 2001.

Jordan et al., "Magnetic fluid hyperthermia (MFH): Cancer treatment with AC magnetic field induced excitation of biocompatible superparamagnetic nanoparticles", Magnetism and Magnetic Materials., 201:413-19, 1999.

Jue et al., "Addition of sulfhydryl groups to *Escherichia coli* ribosomes by protein modification with 2-iminothiolane (methyl 4-mercaptobutyrimidate)", Biochemistry, 17:5399-5406, 1978.

Kempka et al., "Binding, uptake, and transcytosis of ligands for mannose-specific receptors in rat liver: an electron microscopic study", Experimental Cell Research,176, 38-48, 1988.

Keye et al., "Argon Laser Therapy of Endometriosis: A Review of 92 Consecutive Patients" Fertility and Sterility, 47:208-212, 1987.

Kim et al., "Hollow silica spheres of controlled size and porosity by sol-gel processing", J. Am. Ceram. Soc., 74:1987-1992, 1991.

Kim et al., "Photochemical synthesis of gold nanorods" J. Am. Chem. Soc., 124:14316-17, 2002.

Kim et al., "Self-Organization of Large Gold Nanoparticle Arrays", J. Am. Chem. Soc., 123:7955-56, 2001.

Kim et al., "Fabrication of hollow silica aerogel spheres by a droplet generation method and sol-gel processing" J. Vac. Sci., Technol. A., 7:1181-1184, 1989.

Kneipp et al., "Ultrasensitive Chemical Analysis by Raman Spectroscopy", Chem. Rev., 99:2957-75, 1999.

Kolb-Bachofen et al., "Electron microscopic evidence for an asialoglycoprotein receptor on Kupffer cells: localization of lectin-mediated endocytosis", Cell, 29:859-66, 1982.

Kolbeck, "The biomedical applications of protein microspheres", Ph.D. Doctoral Thesis, University of Illinois, Urbana-Champaign, title page and pp. 153, 159-160, 1999.

Korbelik et al., "Photofrin accumulation in malignant and host cell populations of various tumours", British Journal of Cancer, 73:506-513, 1996.

Langer "Drug delivery and targeting", Nature, 392:5-10, 1998.

Larson et al., "Water-Soluble Quantum Dots for Multiphoton Fluorescence Imaging in Vivo", Science, 300:1434-1436, 2003.

Lasic et al., "Liposomes revisited", Science, 267:1275-1276, 1995.

Lee et al., "Delivery of liposomes into cultured KB cells via folate receptor-mediated endocytosis", J. Biological Chemistry, 269:3198-3204, 1994.

Lee et al., "Engineered microsphere contrast agents for optical coherence tomography", Optics Letters, vol. 28, No. 17, pp. 1546-1548, 2003.

Lee et al., "Optical Characterization of Contrast Agents for Optical Coherence Tomography", Proceedings of SPIE, vol. 4967, pp. 129-134, 2003.

Leelarasamee et al., "A method for the preparation of polylactic acid microcapsules of controlled particle size and drug loading", J. Microencapsulation, 5:147-157, 1988.

Leitgeb et al., "Spectral measurement of absorption by spectroscopic frequency-domain optical coherence tomography", Optics Letters, 25:820-22, 2000.

Li et al., "Optical Coherence Tomography: Advanced Technology for the Endoscopic Imaging of Barrett's Esophagus", Endoscopy, vol. 32, pp. 921-930, 2000.

Li et al., "Imaging Needle for Optical Coherence Tomography", Optics Letters, 25:1520-1522, 2000.

Li et al., "On the growth of highly ordered pores in anodized aluminum oxide", Chem. Mater., 10:2470-80, 1998.

Li et al., "Polycrystalline nanopore arrays with hexagonal ordering on aluminum", J. Vac. Sci. Technol. A, 17:1428-31, 1999.

Licha, "Contrast agents for optical imaging", Topics in Current Chemistry, 222:1-29, 2002.

Lin et al., "Measurement of tissue optical properties by the use of oblique-incidence optical fiber reflectometry", Applied Optics, 36:136-43, 1997.

Lin et al., "Intraocular Microsurgery with a Picosecond Nd:YAG Laser", Lasers in Surgery and Medicine, 15:44-53, 1994.

Liu et al., "In vivo measurement of oxygen concentration using sonochemically synthesized microspheres", Biophysical J., 67:896-901, 1994.

Liu et al., "A novel two-step silica-coating process for engineering magnetic nanocomposites", Chem. Mater., 10:3936-40, 1998.

Liz-Marzan et al., "Homogeneous silica coating of vitreophobic colloids", Chem. Commun., 731-32, 1996.

Lvov et al., "Nanoparticle/polyion assembly on microtemplates (lipid tubules and latex spheres)", Colloids and Surfaces B: Biointerfaces, 23:251-256, 2002.

Lvov et al., "Thin film nanofabrication via layer-by-layer adsorption of tubule halloysite, spherical silica, proteins and polycations", Colloids and Surfaces A: Physicohem. Eng. Aspects, 198-200:375-382, 2002.

Marks et al., Nonlinear interferometric vibrational imaging, E-print@arxiv.org/physics/0311071, URL http://www.arxiv.org/abs/physics/0311071, pp. 1-5, 2003.

Marks et al., "Study of an Ultrahigh-Numerical-Aperture Fiber Continuum Generation Source for Optical Coherence Tomography", Optics Letters, 27:2010-2012, 2002.

Marks et al., "Pulse shaping strategies for nonlinear interferometric vibrational imaging optimized for biomolecular imaging", Conference Proceeding: EMBC 2004: 26th Annual International Conference of the Engineering in Medicine and Biology Society (Sep. 1-5, 2004, San Francisco, CA), vol. 2, 7 pages, (accession No. 8255487).

Masuda et al., "Ordered metal nanohole arrays made by a two-step replication of honeycomb structures of anodic alumina", Science, 268:1466-68, 1995.

Mathias et al., "Tumor-selective radiopharmaceutical targeting via receptor-mediated endocytosis of Gallium-67-deferoxamine-folate", J. of Nuclear Medicine, 37:1003-1008, 1996.

McNamara III et al., "Sonoluminescence temperatures during multi-bubble cavitation", Nature, 401:772-775,1999.

Micali et al., "Separation of Scattering and Absorption Contributions in UV/Visible Spectra of Resonant Systems", Anal. Chem., 73:4958-63, 2001.

Minton et al., "The Laser in Surgery. A 23 Year Perspective.", American Journal of Surgery, 151:725-729, 1986.

Mock et al., "Composite plasmon resonant nanowires", Nano Letters, 2:465-69, 2002.

Mock et al., "Shape effects in plasmon resonance of individual colloidal silver nanoparticles", J. Chem. Phys., 116:6755-59, 2002.

Mohwald, "From Langmuir monolayers to nanocapsules", Colloids and Surfaces A: Physicochem. Eng. Aspects, 171:25-31, 2000.

Morgner et al., "Spectrosopic optical coherence tomography", Optics Letters, 25:111-13, 2000.

Nicewarner-Peña et al., "Submicrometer metallic barcodes", Science, 294:137-41, 2001.

Nielsch et al., "Self-ordering regimes of porous alumina: the 10% porosity rule", Nano Letters 2:677-80, 2002.

Novak et al., "Purification of molecularly bridged metallic nanoparticle arrays by centrifugation and size exclusion chromatography", Anal. Chem., 73:5758-61, 2001.

Oldenburg et al., "Light Scattering From Dipole and Quadrupole Nanoshell Antennas", Appl. Phys. Lett., 75:1063-65, 1999.

Pasternack et al., "Resonance Light Scattering: A New Technique for Studying Chromophore Aggregation", Science, 269:935-39, 1995.

Pathak et al., "Detection of squamous neoplasia by fluorescence imaging comparing porfimer sodium fluorescence to tissue autofluorescence in the hamster cheek-pouch model", American Journal of Surgery, 170:423-426, 1995.

Peters, All about Albumin, in Biochemistry, Genetics, and Medical Applications, (Academic Press, New York), 3 pages, 1996.

Pinkerton et al., "Aerosolized fluorescent microspheres detected in the lung using confocal scanning laser microscopy", Microscopy Research and Technique, 26:437-443, 1993.

Pitris et al., "High-resolution imaging of gynecologic neoplasms using optical coherence tomography", Obstetrics & Gynecology, 93: 135-139, 1999.

Pitris et al., "Feasibility of optical coherence tomography for high-resolution imaging of human gastrointestinal tract malignancies", J. Gastroenterol., 35: 87-92, 2000.

Pollack et al., "Circumferential Argon Laser Photocoagulation for Prevention of Retinal Detachment", Eye, vol. 8, pp. 419-422, 1994.

Profio et al., "Transport of light in tissue in photodynamic therapy", Photochemistry and Photobiology, 46: 591-599, 1987.

Prudhomme et al., "Interstitial Diode Laser Hyperthermia in the Treatment of Subcutaneous Tumor", Lasers in Surgery and Medicine, 19:445-450, 1996.

Puliafito et al., "Imaging of macular disease with optical coherence tomography", Ophthalmology, 102: 217-229, 1995.

Puliafito et al., "Optical Coherence Tomography of Ocular Diseases", Slack Inc, Thorofare, N.J., pp. 3-34, 369-374, 1995.

Pusztay et al., "Encagement of Gold Nanoclusters in Crosslinked Resorcinarene Shells", Supramolecular Chemistry, 14:291-94, 2002.

Quaroni et al., "Preparation of Polymer-Coated Functionalized Silver Nanoparticles", J. Am. Chem. Soc., 121:10642-43, 1999.

Russell-Jones, "Use of vitamin $B_{12}$ conjugates to deliver protein drugs by the oral route", Critical Reviews in Therapuetic Drug Carrier Systems, vol. 15, No. 6, pp. 557-586, 1998.

Sadtler et al., "Spherical ensembles of gold nanoparticles on silica: electrostatic and size effects", Chem. Commun., 1604-05, 2002.

Sansdrap et al., "Influence of manufacturing parameters on the size characteristics and the release profiles of nifedipine from poly(DL-lactide-co-glycolide) microspheres", International Journal of Pharmaceutics, 98:157-164, 1993.

Schaefer et al., "Real-Time Digital Signal Processing-Based Optical Coherence Tomography and Doppler Optical Coherence Tomography", IEEE Transactions on Biomedical Engineering, vol. 51, No. 1, pp. 186-190, 2004.

Schaefer "Real-Time, Digital Signal Processing-Based Optical Coherence Tomography and Optical Doppler Tomography", Master Thesis, University of Illinois at Urbana-Champaign, 2001.

Schmitt et al., "Measurement of Optical Properties of Biological Tissues by Low-Coherence Reflectometry", Applied Optics., vol. 32, pp. 6032-6042, 1993.

Schmitt et al., "Subsurface Imaging of Living Skin with Optical Coherence Microscopy", Dermatology, vol. 191, pp. 93-98, 1995.

Schmitt et al., "Optical-coherence tomography of a dense tissue: statistics of attenuation and backscattering", Phys. Med. Biol., 39: 1705-1720, 1994.

Sergeev et al., "In vivo endoscopic OCT imaging of precancer and cancer states of human mucosa", Optics Express, 1: 432-440, 1997.

Sevick-Muraca et al., "Fluorescence-enhanced, near infrared diagnostic imaging with contrast agents", Current Opinion in Chemical Biology, Op. Chem. Biol., 6:642-50, 2002.

Shiga et al., "Preparation of Poly(D,L-lactide) and Copoly(lactide-glycolide) Microspheres of Uniform Size", J. Pharm. Pharmacol., 48:891-895, 1996.

Shipway et al., "Nanoparticle arrays on surfaces for electronic, optical, and sensor applications", ChemPhysChem., 1:18-52, 2000.

Sivak Jr. et al., "High-resolution endoscopic imaging of the GI tract using optical coherence tomography", Gastrointestinal Endoscopy, 51:474-479, 2000.

Slaga et al., "An animal model for oral cancer", J. National Cancer Institute Monographs, 13:55-60, 1992.

Sokolov et al., "Real-Time Vital Optical Imaging of Precancer Using Anti-Epidermal Growth Factor Receptor Antibodies Conjugated to Gold Nanoparticles", Cancer Research, 63:1999-2004, 2003.

Sönnichsen et al., "Drastic reduction of plasmon damping in gold nanorods", Physical Review Letters, vol. 88, No. 7:077402-1 to 077402-4, 2002.

Sönnichsen et al., "Spectroscopy of Single Metallic Nanoparticles Using Total Internal Reflection Microscopy", Appl. Phys. Lett., 77:2949-51, 2000.

Stavens et al., "Encapsulation of Neutral Gold Nanoclusters by Resorcinarenes", Langmuir, 15:8337-39, 1999.

Su et al., "Tumor characterization with dynamic contrast-enhanced MRI using MR contrast agents of various molecular weights", Magnetic Resonance in Medicine, 39:259-269, 1998.

Suslick et al., "Protein Microencapsulation of Nonaqueous Liquids", J. Am. Chem. Soc., 112:7807-7809, 1990.

Suslick et al., "Versatile sonochemical reaction vessels" in Experimental Organometallic Chemistry: A Practicum in Synthesis and Characterization, (A. Wayda, Darensburg MY, eds. ACS Symposium Series, Washington, D.C.), pp. 195-197, 1987.

Suslick, "Sonochemistry", Science, 247: 1439-1445, 1990.

Tanaka et al., "Direct visualization of colloidal gold-bound molecules and a cell-surface receptor by ultrahigh-resolution scanning electron microscopy", J. Microscopy, 161:455-61, 1991.

Tearney et al., "Optical Biopsy in Human Gastrointestinal Tissue Using Optical Coherence Tomography", American Journal of Gastroenterlogy, vol. 92, pp. 1800-1804, 1997.

Tearney et al., "Optical Biopsy in Human Urologic Tissue Using Optical Coherence Tomography", J. Urology, vol. 157, pp. 1915-1919 (reprinted as 11 pages), 1997.

Tearney et al., "Catheter-based optical imaging of a human coronary artery", Circulation, 94: 3013, 1996.

Tearney et al., "High-Speed Phase- and Group-Delay Scanning with a Grating-Based Phase Control Delay Line", Optics Letters, vol. 22, No. 23 :1811-1813, 1997.

Tearney et al., "In vivo endoscopic optical biopsy with optical coherence tomography", Science, 276: 2037-2039, 1997.

Tearney et al., "Rapid acquisition of in vivo biological images by use of optical coherence tomography", Optics Letters, 21: 1408-1410, 1996.

Tearney et al., "Scanning single-mode fiber optic catheter-endoscope for optical coherence tomography", Optics Letters, 21: pp. 543-545, 1996.

Templeton et al., "Monolayer-protected cluster molecules", Acc. Chem. Res., 33:27-36, 2000.

Timmerman et al., "Resorcinarenes" Tetrahedron, 52:2663-704, 1996.

Tkachenko et al., "Multifunctional Gold Nanoparticle-Peptide Complexes for Nuclear Targeting", J. Am. Chem. Soc., 125:4700-4701, 2003.

Toth et al., "Retinal effects of ultrashort laser pulses in the rabbit eye", Investigative Ophthalmology & Visual Science, 36:1910-17, 1995.

Toublan et al., "Magnetically-inducible optical contrast agents for optical coherence tomography", presented at the Optical Society of America Biomedical Topical Meeting, Miami, FL, Apr. 7-10, 2002.

Tripp et al., "Self-assembly of cobalt nanoparticle rings", J. Am. Chem. Soc., 124:7914-15, 2002.

Turkevich et al., "A Study of the Nucleation and Growth Processes in the Synthesis of Colloidal Gold", Faraday Soc., 11:55-75, 1951.

Tuting, "The immunology of cutaneous DNA immunization", Current Opinion in Molecular Therapeutics, vol. 1, No. 2, pp. 216-225, 1999.

Ung et al., "Controlled method for silica coating of silver colloids. Influence of coating on the rate of chemical reactions", Langmuir, 14:3740-48, 1998.

van der Laan et al., "In vitro activity of novel antifolates against human squamous carcinoma cell lines of the head and neck with inherent resistance to methotrexate", Int. J. Cancer, 51:909-914, 1992.

Van Der Smissen et al., "Ligand-induced clustering of asialoglycoprotein receptors on rat hepatocytes at 4° C.", European J. of Cell Biology, 60:122-30, 1993.

Van Der Smissen et al., "Quantitative analysis of clustering on biological membranes: methodology and application to ligand-induced asialoglycoprotein receptor redistribution on rat hepatocytes", European J. of Cell Biology, 69:45-54, 1996.

van der Zande et al., "Colloidal dispersions of gold rods: synthesis and optical properties", Langmuir, 16:451-58, 2000.

Violante et al., "Improved detectability of VX2 carcinoma in the rabbit liver with contrast enhancement in computed tomography", Radiology, 134:237-239, 1980.

Vitkin et al., "Optical and thermal characterization of natural (*Sepia officinalis*) melanin", Photochemistry and Photobiology, 59:455-62, 1994.

Vo-Dinh, "Surface-Enhanced Raman Spectroscopy Using Metallic Nanostructures", Trends in Analytical Chemistry, 17:557-82, 1998.

Wang et al., "Semiconductor quantum dot-labeled microsphere bioconjugates prepared by stepwise self-assembly", Nano Lett., 2:857-861, 2002.

Wang et al., "Use of a Laser Beam with an Oblique Angle of Incidence to Measure the Reduced Scattering Coefficient of a Turbid Medium", Applied Optics, 34:2362-2366, 1995.

Webb et al., "Sonochemically produced fluorocarbon microspheres: a new class of magnetic resonance imaging agent", J. Magnetic Resonance Imaging, 6:675-683, 1996.

Wei et al., "Resorcinarene-encapsulated nanoparticles: building blocks for self-assembled nanostructures", J. Inclusion Phenomenal Macrocyclic Chemistry, 41, 83-86, 2001.

Wei et al., "Synthesis and Characterization of Resorcinarene-Encapsulated Nanoparticles", Mater. Res. Soc., Symp. Proc. Ser., 581:59-63, 1999.

Wei et al., "Tunable Surface-Enhanced Raman Scattering from Large Gold Nanoparticle Arrays", ChemPhysChem., 2:743-45, 2001.

Wong et al., "Sonochemically produced hemoglobin microbubbles", Mat. Res. Soc. Symp. Proc., 372:89-94, 1995.

Xu et al., "Electromagnetic Contributions to Single-Molecule Sensitivity in Surface-Enhanced Raman Scattering", Physical Review E, 62:4318-24, 2000.

Yazdanfar et al., "High Resolution Imaging of in vivo Cardiac Dynamics Using Color Doppler Optical Coherence Tomography", Optics Express, vol. 1, pp. 424-431, 1997.

Yguerabide et al., "Light-scattering submicroscopic particles as highly fluorescent analogs and their use as tracer labels in clinical and biological applications", Analytical Biochemistry, 262:137-56, 1998.

Yu et al., "Gold nanorods: electrochemical synthesis and optical properties", J. Phys. Chem. B, 101:6661-64, 1997.

Zaheer et al., "In vivo near-infrared fluorescence imaging of osteoblastic activity", Nature Biotechnology, 19:1148-54, 2001.

Marks et al., "Interferometric differentiation between resonant Coherent Anti-Stokes Raman Scattering and nonresonant four-wave-mixing processes", arXiv:physics/0403007, pp. 1-8, 2004.

Vinegoni et al., "Nonlinear optical contrast enhancement for optical coherence tomography", Optics Express, vol. 12, No. 2, p. 331-341, 2004.

Kee et al., "Simple approach to one-laser, broadband coherent anti-Stokes Raman scattering microscopy", Optics Letters, vol. 29, No. 23, p. 2701-2703, 2004.

Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.

Gao et al., "Formulation, Characterization, and Sensing Applications of Transparent Poly(vinyl alcohol)-Polyelectrolyte Blends", Chem. Mater., 10, pp. 2481-2489, 1998.

Marks et al., Molecular Species Sensitive Optical Coherence Tomography Using Coherent Anti-Stokes Raman Scattering Spectroscopy, Coherence Domain Optical Methods and Optical Coherence Tomography in Biomedicine VII, Proceedings of SPIE, vol. 4956, pp. 9-13, 2003.

Bredfeldt et al., "Non-linear interferometric vibrational imaging", Conference on Lasers and Electro-optics, CLEO '03, pp. 309-311, 2003.

Vinegoni et al., "Nonlinear optical contrast enhancement for optical coherence tomography", http://www.arxiv.org/abs/physics/0312114, 13 pages (2003).

Zumbusch et al., "Three-dimensional vibrational imaging by coherent anti-Stokes Raman scattering", Phys. Rev. Lett., 82(20), pp. 4142-4145, 1999.

Cheng et al., "An epi-detected coherent anti-Stokes Raman scattering (E-CARS) microscope with high spectral resolution and high sensitivity", J. Phys. Chem, 105(7), pp. 1277-1280, 2001.

Hashimoto et al., "Molecular vibration imaging in the fingerprint region by use of coherent anti-Stokes Raman scattering microscopy with a collinear configuration", Opt. Lett., 25(24), pp. 1768-1770, 2000.

Volkmer et al., "Vibrational imaging with high sensitivity via epidected coherent anti-Stokes Raman scattering microscopy", Phys. Rev. Lett., 87(2):023901-1-4, 2001.

Schmitt et al., "Optical-coherence tomography of a dense tissue: statistics of attenuation and backscattering", Phys. Med. Biol., vol. 39, pp. 1705-1720, (1994).

Tearney et al., "In vivo endoscopic optical biopsy with optical coherence tomography", Science, vol. 276, pp. 2037-2039, (1997).

Fantini et al., "Assessment of the size, position, and optical properties of breast tumors in vivo by noninvasive optical methods", Applied Optics, vol. 37, pp. 1982-1989, 1998.

Faber et al., "Quantitative measurement of attenuation coefficients of weakly scattering media using optical coherence tomography", Optics Express, 12(19), pp. 4353-4365, 2004.

Fujimoto et al., "Optical Coherence Tomography: An Emerging Technology for Biomedical Imaging and Optical Biopsy", Neoplasia, 2(1-2), pp. 9-25, 2000.

Zysk et al., "Computational methods for analysis of human breast tumor tissue in optical coherence tomography images", Journal of Biomedical Optics, 11(5), 054015-1-054015-7, 2006.

Levitz et al., "Determination of optical scattering properties of highly-scattering media in optical coherence tomography images", Optics Express, 12(2), pp. 249-259, 2004.

Morgner et al., "Spectroscopic optical coherence tomography", Optics Letters, 25(2), pp. 111-113, 2000.

Gossage et al., "Texture analysis of optical coherence tomography images: feasibility for tissue classification", Journal of Biomedical Optics, 8(3), pp. 570-575, 2003.

Zvyagin et al., "Refractive index tomography of turbid media by bifocal optical coherence refractometry", Optics Express, 11(25), pp. 3503-3517, 2003.

Gottschalk, "Ein Meßverfahren zur Bestimmung der optischen Parameter biologisher Gewebe in vitro", Dissertation 93 HA 8984, Universität Fridericiana Karlsruhe, 1993.

Bolin, F.P. et al., "Refractive index of some mammalian tissues using a fiber optic cladding method", Applied Optics, 28, pp. 2297-2303, 1989.

Tearney et al., "Determination of the refractive index of highly scattering human tissue by optical coherence tomography", Optics Letters, 20(21), pp. 2258-2260, 1995.

Zysk et al., "Needle-based refractive index measurement using low-coherence interferometry", Optics Letters, 32, pp. 385-387, 2007.

Zysk et al., "Refractive index of carcinogen-induced rat mammary tumours", Phys. Med. Biol., 51, pp. 2165-2177, 2006.

Li et al., "Measurement method of the refractive index of biotissue by total internal reflection", Applied Optics, 35, pp. 1793-1795, 1996.

Knuttel et al., "Spatially confined and temporally resolved refractive index and scattering evaluation in human skin performed with optical coherence tomography", Journal of Biomedical Optics, 5, pp. 83-92, 2000.

Boppart et al., "Optical coherence tomography: feasibility for basic research and image-guided surgery of breast cancer", Breast Cancer Research and Treatment, vol. 84, pp. 85-97, 2004.

Liberman et al., "Palpable breast masses: Is there a role for percutaneous image-guided core biopsy?", American Journal of Roentgenology, vol. 175, pp. 779-787, 2000.

Bolivar et al., "Stereotaxic core needle aspiration biopsy with multiple passes in nonpalpable breast lesions", Acta Radiologica, vol. 39, pp. 389-394, 1998.

Acheson et al., "Histologic correlation of image-guided core biopsy with excisional biopsy of nonpalpable breast lesions", Archives of Surgery, vol. 132, pp. 815-821, 1997.

Pijnappel et al., "The diagnostic accuracy of core biopsy in palpable and non-palpable breast lesions", European Journal of Radiology, vol. 24, pp. 120-123, 1997.

Durduran et al., "Bulk optical properties of healthy female breast tissue", Physics in Medicine and Biology, vol. 47, pp. 2847-2861, 2002.

International Search Report dated Feb. 15, 2007 for International Application No. PCT/US2006/006618, 5 pages.

Marks et al., "Interferometric differentiation between resonant coherent anti-Stokes Raman scattering and nonresonant four-wave-mixing processes", Applied Physics Letters, vol. 85, No. 23, pp. 5787-5789, 2004.

Marks et al., "Nonlinear Interferometric Vibrational Imaging", Physical Review Letters, vol. 92, No. 12, pp. 123905-1-123905-4, 2004.

Boppart et al., "Contrast Enhancement Methods for Optical Coherence Tomography", Biophotonics/Optical Interconnects and VLSI Photonics/WBM Microactivities, 2004 Digest of the Leos Summer Topical Meetings, San Diego, CA, pp. 14-15, 2004.

Marks et al., "Pulse Shaping Strategies for Nonlinear Interferometric Vibrational Imaging Optimized for Biomolecular Imaging", Proceedings of the 26$^{th}$ Annual International Conference of the IEEE EMBS, San Francisco, CA, pp. 5300-5303, 2004.

Bredfeldt et al., "Nonlinear interferometric vibrational imaging of molecular species", Proc. of SPIE, vol. 5321, pp. 149-156, 2004.

Easy Core Biopsy System, Product Brochure, Boston Scientific, 5 pages, 2004.

Yodh et al., "Spectroscopy and Imaging with Diffusing Light," Physics Today, pp. 34-40, 1995.

Roggan et al., in "Laser Induced Interstitial Thermotherapy", Muller, Ed., pp. 39-40,43, 1995.

Ohmi et al., "In Vitro Simultaneous Measurement of Refractive Index and Thickness of Biological Tissue by the Low Coherence Interferometry", IEEE Transactions on Biomedical Engineering, vol. 47, No. 9, pp. 1266-1270, 2000.

Luo et al., "Optical Biopsy of Lymph Node Morphology using Optical Coherence Tomography", Technology in Cancer Research & Treatment, vol. 4, No. 5, pp. 539-547, 2005.

Dehghani et al., "The effects of internal refractive index variation in near-infrared optical tomography: a finite element modelling approach", Physics in Medicine and Biology, 48, pp. 2713-2727, 2003.

Schmitt et al., "Turbulent nature of refractive-index variations in biological tissue", Optics Letters, vol. 21, No. 16, pp. 1310-1312, 1996.

Zysk et al., "Projected index computed tomography", Optics Letters, vol. 28, No. 9, pp. 701-703, 2003.

Easy Core Biopsy System, Product Brochure, Boston Scientific, 4 pages, 2004.

Evans et al., "Coherent anti-Stokes Raman scattering spectral interferometry: determination of the real and imaginary components of nonlinear susceptibility chi(3) for vibrational microscopy", Optics Letters, vol. 29, No. 24, pp. 2923-2925, 2004.

Yoon et al., "Dependence of line shapes in femtosecond broadband stimulated Raman spectroscopy on pump-probe timed delay", J Chem Phys., 122(2), p. 024505, 2005, 20 pages.

Kolomoitsev et al., "New problems of femtosecond time-domain CARS of large molecules", SPIE vol. 1402, pp. 31-43, 1990.

Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.

Invitation to pay additional fees and partial search report dated Apr. 4, 2008 for PCT application No. PCT/US2007/061364.

Huang, D. et al., "Optical Coherence Tomography", Science, 254, 5035, pp. 1178-1181, (1991).

Fercher, A.F. et al., "Optical Coherence Tomography—principles and applications", Institute of Physics Publishing, Reports on Progress in Physics, 66, pp. 239-303, (2003).

Boppart, S.A. et al., "Optical probes and techniques for molecular contrast enhancement in coherence imaging", J. Biomedical Optics, 10(4), pp. 041208-1 thru 041208-14, (2005).

Oldenburg, A.L. et al., "Imaging magnetically labeled cells with magnetomotive optical coherence tomography", Optics Letters, 30, 7, pp. 747-749, (2005).

Oldenburg, A.L. et al., "Selective OCT imaging of cells using magnetically-modulated optical contrast agents", in Proceedings of the Conference on Lasers and Electro-Optics, pp. 405-4-6, (2003).

Kopelman, R. et al., "Multifunctional nanoparticle platforms for in vivo MRI enhancement and photodynamic therapy of a rat brain cancer", J. Magnetism and Magnetic Materials, 293, pp. 404-410, (2005).

Romanus, E. et al., "Magnetic nanoparticle relaxation measurement as a novel tool for in vivo diagnostics", J. Magnetism and Magnetic Materials, 252, pp. 387-389, (2002).

Oldenburg, A.L. et al., "Magnetomotive contrast for in vivo optical coherence tomography", Optics Express, 13, 17, pp. 6597-6614, (2005).

Oh, J. et al., "Detection of magnetic nanoparticles in tissue using magneto-motive ultrasound", Nanotechnology, 17, pp. 4183-4190, (2006).

Joo, C. et al., "Spectral-domain optical coherence phase microscopy for quantitative phase-contrast imaging", Optics Letters, 30, 16, pp. 2131-2133, (2005).

Choma, M.A. et al., "Spectral-domain phase microscopy", Optics Letters, 30, 10, pp. 1162-1164, (2005).

Choma, M.A. et al., "Doppler flow imaging of cytoplasmic streaming using spectral domain phase microscopy", J. Biomedical Optics 11(2), pp. 024014-1 thru 024014-8, (2006).

Sticker, M. et al., "En face imaging of single cell layers by differential phase-contrast optical coherence microscopy", Optics Letters, 27, 13, pp. 1126-1128, (2002).

Sarunic, M.V. et al., "Full-field swept-source phase microscopy", Optics Letters, 31, 10, pp. 1462-1464, (2006).

De la Torre-Ibarra, M.H. et al., "Double-shot depth-resolved displacement field measurement using phase-contrast spectral optical coherence tomography", Optics Express, 14, 21, pp. 9643-9656, (2006).

Vakoc, B.J. et al., "Phase-resolved optical frequency domain imaging", Optics Express, 13, 14, pp. 5483-5493, (2005).

Pedersen, C.J. et al., "Phase-referenced Doppler optical coherence tomography in scattering media", Optics Letters, 30, 16, pp. 2125-2127, (2005).

Ren, H. et al., "Imaging and quantifying transverse flow velocity with the Doppler bandwidth in a phase-resolved functional optical coherence tomography", Optics Letters, 27, 6, pp. 409-411, (2002).

Zhao, Y. et al., "Doppler standard deviation imaging for clinical monitoring of in vivo human skin blood flow", Optics Letters, 25, 18, pp. 1358-1360, (2000).

Ren, H. et al., "Phase-resolved functional optical coherence tomography: simultaneous imaging of in situ tissue structure, blood flow velocity, standard deviation, birefringence, and Stokes vectors in human skin", Optics Letters, 27, 19, pp. 1702-1704, (2002).

Ding, Z. et al., "Real-time phase-resolved optical coherence tomography and optical Doppler tomography", Optics Express, 10, 5, pp. 236-244, (2002).

White, B.R. et al., "In vivo dynamic human retinal blood flow imaging using ultra-high-speed spectral domain optical Doppler tomography", Optics Express, 11, 25, pp. 3490-3496, (2003).

Ren, H. et al, "Real-time in vivo blood-flow imaging by moving-scatterer-sensitive spectral-domain optical Doppler tomography", Optics Letters, 31, 7, pp. 927-929, (2006).

Fang-Yen, C. et al., "Noncontact measurement of nerve displacement during action potential with a dual-beam low-coherence interferometer", Optics Letters, 29, 17, pp. 2028-2030, (2004).

Choma, M.A. et al., "Sensitivity advantage of swept source and Fourier domain optical coherence tomography", Optics Express, vol. 11, No. 18, pp. 2183-2189, (2003).

Leitgeb, R. et al., "Performance of fourier domain vs. time domain optical coherence tomography", Optics Express, 11, 8, pp. 889-894, (2003).

Leitgeb, R.A. et al., "Ultrahigh resolution Fourier domain optical coherence tomography", Optics Express, 12, 10, pp. 2156-2165, (2004).

De Boer, J.F. et al., "Improved signal-to-noise ratio in spectral-domain compared with time-domain optical coherence tomography", Optics Letters, 28, 21, pp. 2067-2069, (2003).

Ralston, T.S. et al., "Phase Stability Technique for Inverse Scattering in Optical Coherence Tomography", International Symposium on Biomedical Imaging, pp. 578-581, (2006).

Yang, C. "Molecular contrast optical coherence tomography: A review", Photochemistry and Photobiology 81, pp. 215-237, (2005).

Kim, J. et al., "Hemoglobin contrast in magnetomotive optical Doppler tomography", Optics Letters, 31, 6, pp. 778-780, (2006).

Oh, J. et al., "Magneto-motive detection of tissue-based macrophages by differential phase optical coherence tomography", Lasers in Surgery and Medicine, 39, pp. 266-272, (2007).

Crecea, V. et al., "Phase-resolved spectral-domain magnetomotive optical coherence tomography", Proc. of SPIE, 6429, pp. 64291X-1 thru 64291X-10, (2007).

Oldenburg, A.L. et al., "Magnetic contrast agents for optical coherence tomography", Proc. of SPIE, 5316, pp. 91-92, (2004).

Oldenburg, A.L. et al., "High-resolution in vivo nanoparticle imaigng using magnetomotive optical coherence tomography", Proc. of SPIE, 6097, pp. 609702-1 thru 609702-11, (2006).

Schmitt, J.M. "OCT elastography: imaging microscopic deformation and strain of tissue", Optics Express, 3, 6, pp. 199-211, (1998).

Gleich, B. et al., "Tomographic imaging using the nonlinear response of magnetic particles", Nature, 435, pp. 1214-1217, (2005).

Anker, J.N. et al., "Magnetically modulated optical nanoprobes", Applied Physics Letters, 82, 7, pp. 1102-1104, (2003).

Harisinghani, M.G. et al., "Noninvasive Detection of Clinically Occult Lymph-Node Metastases in Prostate Cancer", New England J. of Medicine, 348, 25, pp. 2491-2499, (2003).

Arbab, A.S. et al., "In vivo trafficking and targeted delivery of magnetically labeled stem cells", Human Gene Therapy, 15, pp. 351-360, (2004).

Alexiou, C. et al., "Locoregional cancer treatment with magnetic drug targeting", Cancer Research, 60, pp. 6641-6648, (2000).

Winter, P.M. et al., "Molecular imaging of angiogenesis in early-stage atherosclerosis with integrin-targeted nanoparticles", Circulation, 108, pp. 2270-2274, (2003).

Mornet S. et al., "Magnetic nanoparticle design for medical diagnosis and therapy", J. of Materials Chemistry, 14, pp. 2161-2175, (2004).

Kim, J. et al., "Imaging nanoparticle flow using magneto-motive optical Doppler tomography", Nanotechnology, 18, 035504, pp. 1-6, (2007).

Oldenburg, A.L. et al., "Spectral-Domain Magnetomotive OCT Imaging of Magnetic Nanoparticle Biodistribution", Proc. of SPIE, vol. 6847, pp. 684719-1 thru 684719-8, (2008).

Oldenburg, A.L. et al., "Phase-resolved magnetomotive OCT for imaging nanomolar concentrations of magnetic nanoparticles in tissues", Optics Express, 16(15), pp. 11525-11539, (2008).

Oldenburg, A.L. et al., "Optical micro-scale mapping of dynamic biomechanical tissue properties", Optics Express, 16(15), pp. 11052-11065, (2008).

Oldenburg, A.L. et al., "Spectroscopic optical coherence tomography and microscopy", IEEE Journal of Selected Topics in Quantum Electronics, special issue on Biophotonics, 13(6), pp. 1629-1640, (2007).

Zysk, A.M. et al., "Optical coherence tomography: A review of clinical development from bench to bedside", Special section on optical diagnostic imaging from bench to bedside, Journal of Biomedical Optics, 12(5), pp. 051403-1 thru 051403-20, (2007).

Tan, W. et al., "Optical coherence tomography of cell dynamics in three-dimensional tissue models", Optics Express, 14(16), pp. 7159-7171, (2006).

Oldenburg, A.L. et al., "Plasmon-resonant gold nanorods as law backscattering albedo contrast agents for optical coherence tomography", Optics Express, vol. 14, No. 15, pp. 6724-6738, (2006).

Senin, A.A. et al., "Molecular dissociation observed with an atomic wavepacket and parametric four-wave mixing", Chemical Physics Letters, 381, pp. 53-59, (2003).

Oldenburg, A.L. et al., "Fast Fourier-domain delay line for in vivo optical coherence tomography with a polygonal scanner", Applied Optics, 42(22), pp. 4606-4611, (2003).

Marks, D.L. et al., "Autofocus algorithm for dispersion correction in optical coherence tomography", Applied Optics, 42(16), pp. 3038-3046, (2003).

Marks, D.L. et al., "Digital algorithm for dispersion correction in optical coherence tomography for homogeneous and stratified media", Applied Optics, vol. 42, No. 2, pp. 204-217, (2003).

Oldenburg, A.L. et al., "Vibrational wave packets in the $B^1\Pi_u$ and $D^1\Sigma u^+$ states of Cs2: Determination of improved Cs2+(X) and Cs2(B) spectroscopic constants", Journal of Chemical Physics, 113(24), pp. 11009-11018, (2000).

Oldenburg, A.L. et al., "Optically pinpointing magnetic nanoparticles within biological tissue", Optics & Photonics News, 17(12), p. 24, (2006).

Nguyen, F.T. et al., "Magnetic protein microspheres as dynamic contrast agents for magnetomotive optical coherence tomography", Proc. of SPIE, 6867, pp. 68670F-1 thru 68670F-11, (2008).

Oldenburg, A.L. et al., "Plasmon-resonant gold nanorods provide spectroscopic OCT contrast in excised human breast tumors", Proc. of SPIE, 6867, pp. 68670E-1 thru 68670E-10, (2008).

Oldenburg, A.L. et al., "Spectral-domain magnetomotive OCT imaging of magnetic nanoparticle biodistribution", Proc. of SPIE, 6847, pp. 684719-1 thru 684719-11, (2008).

Liang, X. et al., "Modeling and measurement of tissue elastic moduli using optical coherence elastography", Proc. of SPIE, 6858, pp. 685803-1 thru 685803-8, (2008).

Oldenburg, A.L. et al., "Backscattering albedo contrast in OCT using plasmon-resonant gold nanorods", Proc. of SPIE, 6429, pp. 64291Z-1 thru 6429Z-8, (2007).

Oldenburg, A.L. et al., "Characterization of plasmon-resonant gold nanorods as near-infrared optical contrast agents investigated using a double-integrating sphere system", Proc. of SPIE, 5703, pp. 50-60, (2005).

Oldenburg, A.L. et al., "Magnetic contrast agents for optical coherence tomography." Proc. of SPIE, 5316, pp. 91-98, (2004).

Oldenburg, A.L. et al., "Optical manipulation of silicon microparticles in biological environments", Proc. of SPIE, 4962, pp. 249-255, (2003).

Oldenburg, A.L., "Wavepacket dynamics and time-domain spectroscopy in atomic rubidium", Quantum Electronics and Laser Science Conference 1999, Technical Digest, Thursday Morning, pp. 176-177, (1999).

Swanson, E.A. et al., "In vivo retinal imaging by optical coherence tomography", Optics Letters, 18, 21, pp. 1864-1866, (1993).

American Academy of Pediatrics, Clinical Practice Guideline, "Otitis Media with Effusion", Pediatrics, 113, 5, pp. 1412-1429, (2004).

Pitris, C. et al., "High-resolution imaging of the middle ear with optical coherence tomography: A feasibility study," Arch Otolaryngol Head Neck Surg., 127, pp. 637-642, (2001).

Hall-Stoodley, L. et al., "Direct detection of bacterial biofilms on the middle-ear mucosa of children with chronic otitis media," JAMA, 296, 2, pp. 202-211, (2006).

Xi, C. et al., "High-resolution three-dimensional imaging of biofilm development using optical coherence tomography," J. Biomed. Opt., 11(3), pp. 034001-1 thru 034001-6, (2006).

Leitgeb, R. et al., "Performance of Fourier domain vs. time domain optical coherence tomography," Optics Express, 11, 8, 889-894, (2003).

Ralston, T.S. et al., "Interferometric synthetic aperture microscopy", Nature Physics, 3, pp. 129-134, (2007).

Ralston, T.S. et al., "Inverse Scattering for Optical Coherence Tomography", J. Opt. Soc. Am. A, 23, 5, pp. 1027-1037, (2006).

Sitter, D.N. et al., "Three-dimensional Imaging: a Space invariant Model for Space Variant Systems", Applied Optics, 29, 26, pp. 3789-3794, (1990).

Choma, M.A. et al., "Sensitivity advantage of swept source and Fourier domain optical coherence tomography", Optics Express, 11, 18, pp. 2183-2189, (2003).

Ralston, T.S. et al., "Phase Stability Technique for Inverse Scattering in Optical Coherence Tomography", Biomedical Imaging: Nano to Macro, 3rd IEEE International Symposium on Biomedical Imaging, pp. 578-581, (2006).

Costerton, J.W. et al., "Bacterial biofilms: a common cause of persistent infections", Science, 284, pp. 1318-1322, (1999).

Donlan, R.M., "Biofilms and device-associated infections", Emerging Infectious Diseases, 7, 2, pp. 277-281, (2001).

Donlan, R.M. "Biofilms: microbial life on surfaces", Emerging Infectious Diseases, 8, 9, pp. 881-890, (2002).

Fux, C.A. et al., "Survival strategies of infectious biofilms", Trends in Microbiology, 13, 1, pp. 34-40, (2005).

Takata, G.S. et al., "Evidence Assessment of the Accuracy of Methods of Diagnosing Middle Ear Effusion in Children With Otitis Media With Effusion", Pediatrics, 112, 6, pp. 1379-1387, (2003).

Reed, W.A. et al., "Gradient-index fiber-optic microprobes for minimally invasive in vivo low-coherence interferometry," Optics Letters, 27, 20, pp. 1794-1796, (2002).

Vinegoni, C. et al., "Integrated structural and functional optical imaging combining spectral-domain optical coherence and multiphoton microscopy", Applied Physics Letters, 88, pp. 053901-1 thru 053901-3, (2006).

Crecea, V., "Phase-resolved spectral-domain magnetomotive optical coherence tomography for microscopic analysis of biomechanical properties", Preliminary Examination, pp. 1-15, (2007).

Xu, C. et al., "Near-infrared dyes as contrast-enhancing agents for spectroscopic optical coherence tomography", Optics Letters, vol. 29, No. 14, pp. 1657-1649, (2004).

Nguyen, F.T. et al., "Portable Real-Time Optical Coherence Tomography System for Intraoperative Imaging and Staging of Breast Cancer", Proc. of SPIE, vol. 6430, pp. 64300H-1 thru 64300H1-10, (2007).

Zysk, A.M. et al., "Needle-probe system for the measurement of tissue refractive index", Proc. of SPIE, vol. 6430, pp. 64300O-1-64300O-8, (2007).

Pasquesi, J.J. et al., "Detection of ultrastructural changes in genetically-altered and exercised skeletal muscle using PS-OCT", Proc. of SPIE, vol. 6079, pp. 607926-1-607926-7, (2006).

Xu, C. et al., "Spectroscopic spectral-domain optical coherence microscopy", Optics Letters, vol. 31, No. 8, pp. 1079-1081, (2006).

Jones, G.W. et al., "High-spectral-resolution coherent anti-stokes raman scattering with interferometrically detected broadband chirped pulses", Optics Letters, vol. 31, No. 10, pp. 1543-1545, (2006).

Boppart, S.A., "Advances in contrast enhancement for optical coherence tomography", Proceedings of the 28th IEEE EMBS Annual International Conference New York City, USA, pp. 121-124, Aug. 30-Sep. 3, 2006.

Marks, D.L. et al., "High numerical aperture full-field optical coherence tomography with space-invariant resolution without scanning the focus", Proc. of SPIE, vol. 6429, pp. 64291R1-64291R-9, (2007).

Luo, W. et al., "Three-dimensional optical coherence tomography of the embryonic murine cardiovascular system", Journal of Biomedical Optics, vol. 11(2), pp. 021014-1-021014-8, (2006).

Marks, D.L. et al., "Inverse scattering for frequency-scanned full-field optical coherence tomography", Journal of the Optical Society of America A, vol. 24, No. 4, pp. 1034-1041, (2007).

Ralston, T.S. et al., "Inverse scattering for high-resolution interferometric microscopy", Optics Letters, vol. 31, No. 24, pp. 3585-3587, (2006).

Ralston, T.S. et al., "Demonstration of inverse scattering in optical coherence tomography", Proc. of SPIE, vol. 6079, pp. 60791T-1-60791T-9, (2006).

Marks, D.L. et al., "Inverse scattering for rotationally scanned optical coherence tomography", J. Opt. Soc. Am. A, vol. 23, No. 10, pp. 2433-2439, (2006).

Zysk, A.M. et al., "Needle-based reflection refractometry of scattering samples using coherence-gated detection", Optics Express, vol. 15, No. 8, pp. 4787-4794, (2007).

Pasquesi, J.J. et al., "In vivo detection of exercise-induced ultrastructural changes in genetically-altered murine skeletal muscle using polarization-sensitive optical coherence tomography", Optics Express, vol. 14, No. 4, pp. 1547-1556, (2006).

Ko, H.J. et al., "Optical coherence elastography of engineered and developing tissue", Tissue Engineering, vol. 12, No. 1, pp. 63-73, (2006).

Zhu, C. et al., "Use of a multiseparation fiber optic probe for the optical diagnosis of breast cancer", Journal of Biomedical Optics, vol. 10(2), p. 024032-1-024032-13, (2005).

Bigio, I.J. et al., "Diagnosis of breast cancer using elastic-scattering spectroscopy: preliminary clinical results", Journal of Biomedical Optics, vol. 5, No. 2, pp. 221-228, (2000).

Bitar, R.A. et al., "Biochemical analysis of human breast tissues using Fourier-transform Raman spectroscopy", Journal of Biomedical Optics, vol. 11(5), p. 054001-1-054001-8, (2006).

Demos, S.G. et al., "Investigation of near-infrared autofluorescence imaging for the detection of breast cancer", IEEE Journal of Selected Topics in Quantum Electronics, vol. 11, No. 4, pp. 791-798, (2005).

Demos, S.G. et al., "Advances in optical spectroscopy and imaging of breast lesions", Journal of Mammary Gland Biology and Neoplasia, vol. 11, pp. 165-181, (2006).

Fournier, L.S. et al., "In-vivo NIR autofluorescence imaging of rat mammary tumors", Optics Express, vol. 14, No. 15, pp. 6713-6723, (2006).

Frank, C.J. et al., "Characterization of human breast biopsy specimens with near-IR Raman-spectroscopy", Analytical Chemistry, vol. 66, No. 3, pp. 319-326, (1994).

Gupta, P.K. et al., "Breast cancer diagnosis using $N_2$ laser excited autofluorescence spectroscopy", Lasers in Surgery and Medicine, vol. 21, pp. 417-422, (1997).

Haka, A.S. et al., "Identifying microcalcifications in benign and malignant breast lesions by probing differences in their chemical composition using Raman spectroscopy", Cancer Research, vol. 62, pp. 5375-5380, (2002).

Haka, A.S. et al., "Diagnosing breast cancer by using Raman spectroscopy", Proceedings of the National Academy of Sciences of the United States of America, vol. 102, No. 35, pp. 12371-12376, (2005).

Haka, A.S. et al., "In vivo margin assessment during partial mastectomy breast surgery using Raman spectroscopy", Cancer Research, vol. 66, pp. 3317-3322, (2006).

Iftimia, N.V. et al., "A portable, low coherence interferometry based instrument for fine needle aspiration biopsy guidance", Review of Scientific Instruments, vol. 76, p. 064301-1-064301-6, (2005).

Lenkinski, R.E. et al., "Near-infrared fluorescence imaging of microcalcification in an animal model of breast cancer", Academic Radiology, vol. 10, pp. 1159-1164, (2003).

Manoharan, R. et al., "Raman spectroscopy and fluorescence photon migration for breast cancer diagnosis and imaging", Photochemistry and Photobiology, vol. 67(1), pp. 15-22, (1998).

Motz, J.T. et al., "Optical fiber probe for biomedical Raman spectroscopy", Applied Optics, vol. 43, No. 3, pp. 542-554, (2004).

Palmer, G.M. et al., "Diagnosis of breast cancer using optical spectroscopy", Medical Laser Application, vol. 18, pp. 233-248, (2003).

Palmer, G.M. et al., "Comparison of multiexcitation fluorescence and diffuse reflectance spectroscopy for the diagnosis of breast cancer", IEEE Transactions on Biomedical Engineering, vol. 50, No. 11, pp. 1233-1242, (2003).

Peters, V.G. et al., "Optical properties of normal and diseased human breast tissues in the visible and near infrared", Physics in Medicine and Biology, vol. 35, No. 9, pp. 1317-1334, (1990).

Redd, D.C.B. et al., "Raman spectroscopic characterization of human breast tissues: Implications for breast cancer diagnosis", Applied Spectroscopy, vol. 47, No. 6, pp. 787-791, (1993).

Shafer-Peltier, A.S. et al., "Raman microspectroscopic model of human breast tissue: implications for breast cancer diagnosis in vivo", Journal of Raman Spectroscopy, vol. 33, pp. 552-563, (2002).

Shah, N. et al., "Noninvasive functional optical spectroscopy of human breast tissue", Proceedings of the National Academy of Sciences of the United States of America, vol. 98, No. 8, pp. 4420-4425, (2001).

Shetty, G. et al., "Raman spectroscopy: elucidation of biochemical changes in carcinogenesis of oesophagus", British Journal of Cancer, vol. 94, pp. 1460-1464, (2006).

Yang, Y. et al., "Fundamental differences of excitation spectrum between malignant and benign breast tissues", Photochemistry and Photobiology, vol. 66(4), pp. 518-522, (1997).

Zysk, A.M. et al., "Optical coherence tomography: a review of clinical development from bench to bedside", J. Biomedical Optics, 12(5), pp. 051403-1 thru 051403-21, (2007).

Choi, J.H. et al., "Multimodal biomedical imaging with asymmetric single-walled carbon nanotube/iron oxide nanoparticle complexes", Nano Letters, vol. 7, No. 4, pp. 861-867, (2007).

Zysk, A.M. et al., Comment on "In vivo cancer diagnosis with optical spectroscopy and acoustically induced blood stasis using a murine Mca35 model", Medical Physics, vol. 34, Issue 3, p. 1130, (2007).

Boppart, M.D. et al., "$\alpha_7 \beta_1$- Integrin regulates mechanotransduction and prevents skeletal muscle injury", American Journal of Physiology: Cell Physiology, vol. 290, Issue 6, pp. C1660-C1665, (2006).

Toublan, F.J-J. et al., "Tumor targeting by surface-modified protein microspheres", Journal of the American Chemical Society, vol. 128, Issue 11, pp. 3472-3473, (2006).

Vinegoni, C. et al., "Integrated structural and functional optical imaging combining spectral-domain optical coherence and multiphoton microscopy", Applied Physics Letters, vol. 88, Issue 5, pp. 053901-1 thru 053901-3, (2006).

Vinegoni, C. et al., "Multi-modality imaging of structure and function combining spectral-domain optical coherence and multiphoton microscopy", Proc. of SPIE, vol. 6079, pp. 60791D-1 thru 60791D-8, (2006).

Boppart, S.A. et al., "Real-time optical biopsy and analysis of breast cancer using clinical optical coherence tomography", Journal of Clinical Oncology, Abstract presentation from the 2007 ASCO Annual Meeting Proceedings Part 1, vol. 25, No. 18S, (2007).

American Cancer Society, "2007 Cancer facts & figures", 56 pages, (2007).

Boppart, S.A. et al., "Optical coherence tomography: feasibility for basic research and image-guided surgery of breast cancer", Breast Cancer Research and Treatment, vol. 84, pp. 85-97, (2004).

Berg, W.A. et al., "Diagnostic accuracy of mammography, clinical examination, US, and MR imaging in preoperative assessment of breast cancer", Radiology, vol. 233, pp. 830-849, (2004).

Kawasaki, M., et al., "Diagnostic accuracy of optical coherence tomography and integrated backscatter intravascular ultrasound images for tissue characterization of human coronary plaques", Journal of the American College of Cardiology, vol. 48, No. 1, pp. 81-88, (2006).

Oldenburg, A.L. et al., "Molecular OCT contrast enhancement and imaging", Optical Coherence Tomography: Technology and Applications, Ch. 24, (2008).

Oldenburg, A.L. et al., "Optical coherence tomography", McGraw-Hill Encyclopedia of Science & Technology, (2005).

Oldenburg, A.L et al., "Imaging gold nanorods in excised human breast carcinoma by spectroscopic optical coherence tomography", Journal of Materials Chemistry, (2009).

* cited by examiner (Michelson-type Interferometer)

(Amplitude OCT Image)

MAGNETOMOTIVE OPTICAL COHERENCE TOMOGRAPHY

CROSS REFERENCE To RELATED APPLICATION

This application claims the benefit of U.S. Provisional Application No. 61/022,276 filed 18 Jan. 2008.

FEDERALLY SPONSORED RESEARCH OR DEVELOPMENT

This invention was made with government support under grant/contract no. BES05-19920 awarded by the National Science Foundation, and under grant/contract no. 1 R21 EB005321 awarded by the National Institutes of Health. The government has certain rights in the invention.

BACKGROUND

Optical coherence tomography (OCT) is a novel biomedical imaging technique that can render 2D and 3D structural and functional information in real time.[1,2] OCT is based on the theory of low-coherence interferometry. Biological samples absorb very little and scatter some of the near infrared light (NIR) that they are probed with.[2] OCT uses NIR to probe specimens as deep as a few millimeters, with micron resolution. OCT systems have been introduced recently in a clinical setting for use in ophthalmology.

In OCT the NIR probing light is equally split into a mirror arm that serves as a reference and a sample arm. The interference of the backscattered light fields in the two arms of the interferometer ($E_r$ and $E_s$) is detected (as intensity $I_d$) and used to determine the structure of the scattering object in the sample arm. Image reconstruction is based on the theory of inverse scattering; by inverse Fourier-transforming the autocorrelation signal from the demodulated detected intensity at different times (time-domain OCT, or TD-OCT, FIG. 1) or wavelengths (spectral-domain OCT, or SD-OCT; also commonly referred to as Fourier domain OCT), one can retrieve the complex analytic signal that contains amplitude and phase information about the object. For interference to occur in TD-OCT the optical paths of the reference and the sample arms need to differ by no more than the coherence length $I_c$ of the source. This also sets the limit on the axial resolution of the system, which is equal to $I_c$. For a Gaussian probing spectrum, $I_c$ is inversely proportional to the bandwidth $\Delta\lambda$ of the source. Therefore, the use of a very broad bandwidth source for high axial resolution imaging is desired. The transverse resolution $R_T$ is given by the diameter of the probing beam $2w_0$ and can be expressed in terms of the focal length f of the collimator, the center wavelength of the source $\lambda_0$, and the diameter of the focused beam D, as shown below (assuming a Gaussian probing beam).

$$I_d(t) = \frac{(I_r + I_s)}{2} + \text{Re} < E_r^*(t+\tau)E_s(t) >$$

$$l_c = \frac{2\ln 2}{\pi}\frac{\lambda_0^2}{\Delta\lambda} \approx 0.44\frac{\lambda_0^2}{\Delta\lambda}$$

$$R_T = 2w_0 \approx 2.44\frac{f\lambda_0}{D}$$

Superparamagnetic iron oxide (SPIO) particles have been used extensively as contrast agents for magnetic resonance imaging (MRI).[9] Magnetic particles with small core sizes (<100 nm) are easily transported through the circulatory system and are able to extravasate, and are thus suitable for both in vivo and in vitro studies.[6,8] Depending on their composition and size, magnetic particles can be very responsive to external, non-invasive manipulation or detection due to their strong magnetic susceptibility. Moreover, they can be functionalized to target antigens and thus enhance contrast at the molecular and cellular level, aiding in pathogen localization and early diagnosis of disease. The use of these magnetic particles in OCT has several advantages: the ability to externally manipulate the particles, the low magnetic susceptibility inherent in human tissues, the availability of FDA approved biocompatible iron oxide particles for MRI contrast, and the potential for hyperthermic therapy with high frequency (>100 kHz) modulation.

Magnetomotive optical coherence tomography (MM-OCT) in a time-domain optical coherence tomography (TD-MMOCT) system has been used for detecting the displacements in different samples caused by the modulation of the magnetic field and it has been subsequently shown that the magnetomotive response in the system is predictable.[8] In this scheme, axial scans in a two-dimensional transversal sample plane are acquired with the magnetic field off and on, while allowing the particles and the sample sufficient time to complete motion and reach equilibrium between axial scans, for example at a line rate of 10 Hz. Thus, the images taken with the TD-MMOCT system represent a static description of the sample in the absence and in the presence of the magnetic field, and may be used as a background-rejecting method by estimating a background displacement signal when the magnetic field is off, compared to the magnetic-specific displacement when the magnetic field is off-on.[8]

This previous work demonstrated the ability to image magnetite ($Fe_3O_4$) micro-and nanoparticles after uptake by in vitro macrophages[4] and in vivo African frog tadpoles[8] by modulating an externally applied magnetic field and detecting the resultant magnetomotion specific to the particles. Other researchers have also used this principle to provide hemoglobin contrast in optical Doppler tomography,[31] and to detect iron uptake in tissues with differential phase OCT[32] and also in ultrasound.[9]

Phase measurements in common-path low-coherence light interferometry have been shown to render high sensitivity to sub-wavelength displacements or obstacles in the path of light.[10-12] Path length sensitivities as low as 25 m for spectral-domain optical coherence phase microscopy (SD-OCPM)[10] and 18 m (equivalent phase stability=0.4 mrad) for spectral-domain phase microscopy (SDPM)[11] have been reported. Phase-resolved methods[10-15] are often used in a dynamical regime, such as in measuring intralipid[16-18] or blood flow[19-23] velocities, nerve displacements,[24] or monitoring cell[10] and even cardiomyocyte[12] activity.

SUMMARY

In a first aspect, the present invention is a spectral-domain magnetomotive optical coherence tomography apparatus, comprising (a) a spectral-domain optical coherence tomography device, and (b) a magnet. The magnet is coupled with the optical coherence tomography device so that changes in the magnetic field are coordinated with collection of data by the optical coherence tomography device.

In a second aspect, the present invention is a method of examining a sample, comprising examining the sample with a spectral-domain optical coherence tomography device, to collect data. The sample comprises magnetic particles, and the magnetic particles are subjected to a changing magnetic field during the examining.

DEFINITIONS

The following definitions are included to provide a clear and consistent understanding of the specification and claims.

The signal-to-noise ratio (SNR) is defined as the integrated intensity at $f_B$ compared to a control sample.

A "tissue phantom" or simply "phantom" is a synthetic control sample intended to mimic tissue when examined by OCT.

"Spectral-domain optical coherence tomography" or "SD-OCT" is any type of optical coherence tomography where a Fourier transform of the collected data is required to obtain temporal interference data or a temporal interferogram. SD-OCT is distinct from time-domain optical coherence tomography (TD-OCT) where a Fourier transform of the collected data is not required to obtain temporal interference data.

The term "substantially parallel" means parallel and up to 5° from parallel.

DETAILED DESCRIPTION

Figure 1:
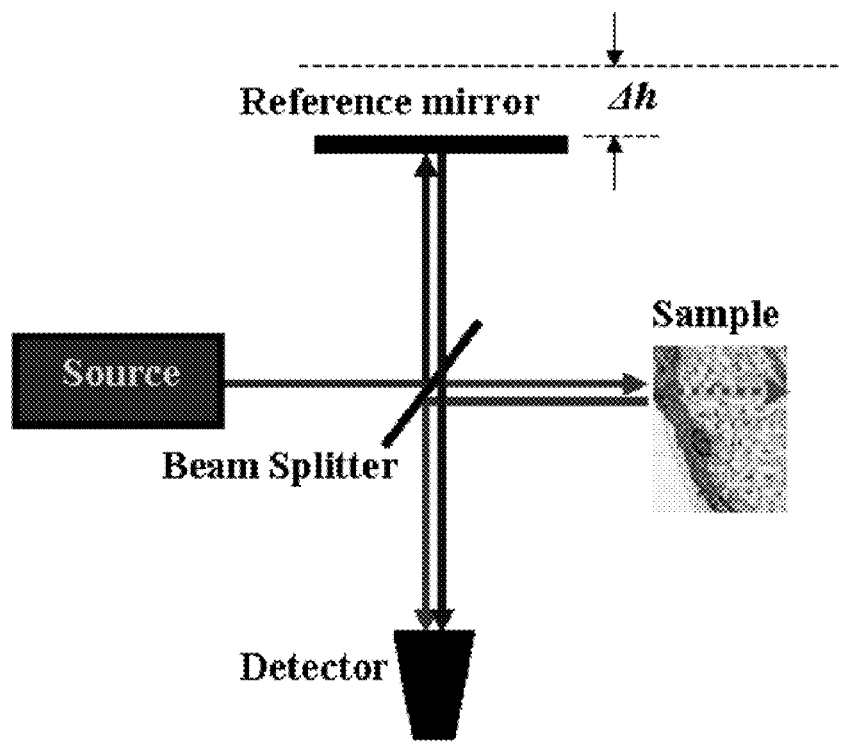
FIG. 1 is a schematic of a Michelson-type interferometer set-up for time-domain OCT.

The present invention is based on the discovery of a method and apparatus for imaging a sample (such as biological tissue, in vivo and/or in vitro) which contains magnetic particles (more specifically, particles with a high magnetic susceptibility, such as magnetite and maghemite) that may be used to induce movement in the tissue at the location of the particle. This is referred to as magnetomotive imaging. The particles are referred to as a "contrast agents", although typically there is no imaging of the particles themselves; typically, the particles do not themselves scatter light. The imaging is carried out using OCT, preferably SD-OCT (which may be referred to as spectral-domain magnetomotive optical coherence tomography, SD-MMOCT). This technique may be used to image biological tissue, with microscopic resolution and millimeter scale or larger imaging volumes. The imaging of the particles is carried out by placing a magnet, preferably an electromagnet, near the sample surface to be scanned (biological or non-biological) and modulating the magnetic field, for example by modulating the current to the electromagnet, or by rotating or moving a permanent magnet, during imaging. The magnetic field gradient produced by the magnet pulls/pushes the magnetic particles toward/away from the magnet, and in doing so displaces them from their rest positions (for example, where they are bound to the surface of a diseased biological cell that has been targeted). These nano- or micro-scale displacements are modulated at the same frequency as the magnetic field, and are detected by the OCT system as a change in scattering by the environment immediately surrounding the particles.

Imaging light is preferably transversely scanned slowly, so that multiple modulations of the magnetic field are accomplished over the time it takes the imaging system to collect the data over one transverse resolution distance. A subsequent image in the same location is acquired with the magnetic field off, allowing for the contribution of background motions to be subtracted from the original image, and thus an image of the distribution of the particles is rendered. When using a SD-OCT system, the magnetomotive signal is dominated by a phase modulation in the OCT data, which is more sensitive than amplitude modulation.

The magnetic particles can be selected for biological or non-biological applications. For biological applications, the magnetic particles are preferably polymer-coated to make them biocompatible. The magnetic particles may be targeted using a variety of techniques: (1) the magnetic particles may be targeted for specific disease markers expressed by biological cells, by labeling the surfaces of the particles with antibodies, peptides, or other proteins that have specificity for the markers;[42] (2) the magnetic particles may be passively targeted using features of the disease, for example, the additional blood vasculature present in tumors; and/or (3) the magnetic particles may be manipulated into certain areas (such as the body of a patient, or location within a sample) using an external magnetic field, (this method is known as magnetic drug targeting: for instance, collection of particles at the site of a mass for both imaging and treatment).[41]

Examples of these types of particles include SPIOs (Superparamagnetic Iron Oxides) and USPIOs (Ultrasmall Superparamagnetic Iron Oxide), which have been used as MRI contrast agents for several purposes, including prostate cancer detection by the specific uptake of SPIOs by healthy lymph nodes.[39] Examples of these commercially available magnetic particles include FERIDEX I.V.® (ferumoxides injectable solution, Bayer HealthCare Pharmaceuticals), RESOVIST® (SH U 555 A; Schering, Berlin, Germany), and COMBIDEX® (ferumoxides, USPIO, Advanced Magnetics).

Hyperthermic therapy may be used to killing cells, such as cancer cells, with the magnetic particles, once they have reached the desired site.[43] Furthermore, because these magnetic particles were developed originally for MRI, they may also be used for multimodal imaging: by injecting the magnetic particles in a patient or live animal, the particles can be traced over several hours or up to several days using both the MRI and OCT. This invention thus allows for the distribution of the particles to be imaged on the microscopic scale, which can be used concomitantly with MRI, and also with hyperthermic therapy.

In one specific application, a patient may be exposed to magnetic iron oxide particles targeting cancer, imaged with MRI to determine general regions of disease, then during surgical intervention the mesoscale imaging provided by this device would provide the surgeon with microscale images of the locations of the magnetic particles. Because OCT imaging in particular typically penetrates a few millimeters below the tissue surface, this would allow the surgeon to evaluate the surgical margins of, for example, a cancerous tumor.

This OCT system may also be used for elastography, to measure the stiffness of the tissue (elastic modulus) and/or the viscosity of the tissue. There are several ways to carry out elastography using OCT: (1) the magnetic field is rapidly switched on or off, and the resulting relaxation oscillations of the tissue are recorded; this decay signal contains the resonant frequency of the tissue (which is proportional to the square root of the elastic modulus) and the decay time of the tissue (which is proportional to the viscosity); and (2) the magnetic field is square-root sinusoidally modulated (to provide a sinusoidal force), and the frequency of modulation is chirped to cover a range of frequencies; the response of the tissue contains the frequency-dependent amplitude and phase of particle displacement (note: this is a different phase than the optical phase described above). These amplitude and phase changes versus frequency are mapped to the viscosity and elastic modulus of the tissue. Preferably, when carrying out the method of (1) or (2), an identical analysis is carried out on a homogeneous control sample having a known viscosity and/or known elastic modulus.

A changing magnetic field may be produced using an electromagnet, preferably cooled using a water-jacket attached to a chiller. Alternatively, one or more permanent magnets, which may be rotated or moved, may also be used to produce a changing magnetic field. In another aspect, the magnet could be an electromagnet within a catheter for insertion within the sample, such as a patient.

In order to study the dynamics of motion in tissue, we chose to take advantage of the capabilities of a SD-OCT system: fast acquisition rates, good phase stability for increased sensitivity of detection (the reference-arm mirror is fixed, unlike in TD-OCT systems), and not least, better signal to noise ratios.[25-28] Using the faster axial line rates ($\geq$1 kHz) of SD-OCT, magnetomotion is dynamic,[33] and thus provides a new method which does not require excessive dwelling at each tissue location.

Figure 3:
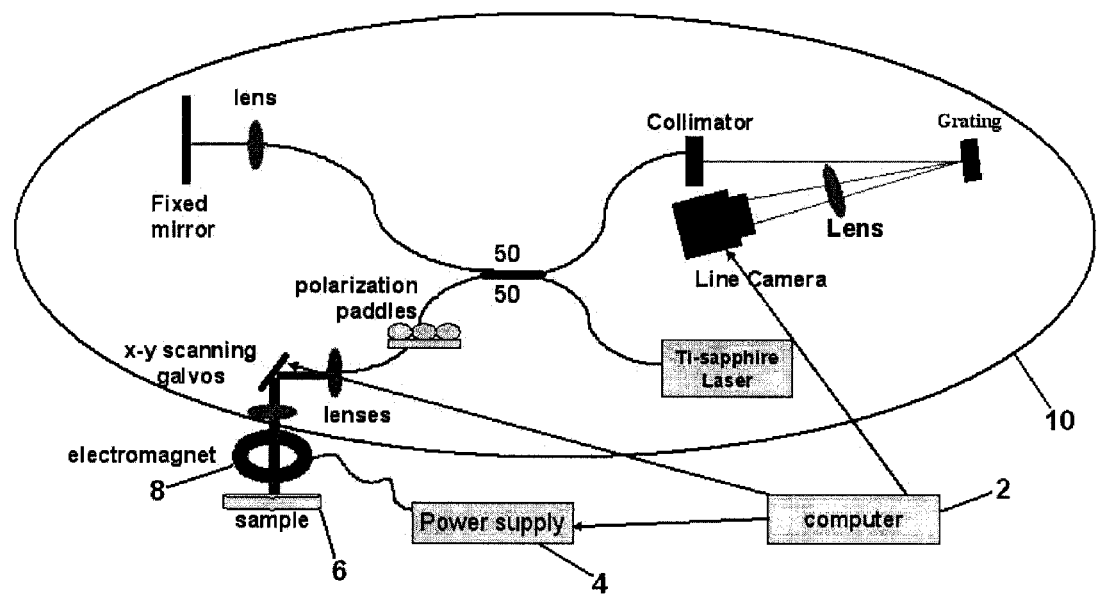
FIG. 3 is a diagram of an experimental set-up for spectral-domain MMOCT.

An aspect of the present invention includes an SD-MMOCT apparatus, illustrated in FIG. 3. The apparatus includes a SD-OCT device, 10. The specifics of the device used in the examples are described in that section, but any SD-OCT device may be used. The apparatus also includes an electromagnet, 8, preferably arranged so that the dominant gradient of the magnetic field it produces in aligned with the axial scanning direction of the SD-OCT device; preferably, the electromagnet allows the light from the SD-OCT device to pass through it. The electromagnet is powered by a power supply, 4, to which it is electrically connected, and optionally one or more computers, 2, are connected to the SD-OCT device and the power supply, for controlling and directing them, and for storing and processing the data collected by the SD-OCT. Also illustrated in FIG. 3 is a sample, 6, which is arranged for scanning by the SD-OCT device and near enough to the electromagnet to be subjected to the magnetic field produced.

The SD-OCT device includes a detector, such as a line camera. Preferably, the line rate of the detector is greater than $2f_B$; this is known as the Nyquist sampling criterion. In an aspect of the present invention, the SD-OCT will include a swept source, rather than the typical broadband source. In another aspect of the present invention, the SD-OCT is a common-path interferometer.

In TD-OCT the time-dependent signal measured, $S_{OCT}(T)$, is:

$$S_{OCT}(\tau) = \langle \text{Re}(E^*_{sample}(t)E_{ref}(t-\tau))\rangle$$

$$\tilde{S}_{OCT}(\tau) = Hilbert\{S_{OCT}(\tau)\}$$

$$= S_{env}(\tau)e^{i\phi(\tau)}$$

where $E_{sample}$ and $E_{ref}$ are the electric fields from the sample and reference arms, respectively, and $\tau$ is the delay time from the moving mirror. The complex analytic signal $\tilde{S}_{OCT}$ is obtained by the Hilbert transformation, and can be written in terms of a slowly-varying envelope $S_{env}$ and fast-modulated phase $\phi$ (which are positive and real-valued numbers). Typically the OCT image is constructed from $S_{env}$ alone.

In SD-OCT the frequency-dependent signal measured is:

$$S_{OCT}(\omega) = \langle E^*_{sample}(\omega)E_{ref}(\omega)\rangle$$

$$\tilde{S}_{OCT}(\tau) = \text{Fourier}\{S_{OCT}(\omega)\}$$

and the complex analytical time-domain signal $\tilde{S}_{OCT}$ is obtained by Fourier transformation of the data. This relationship is known as the Wiener-Khintchine theorem.

When embedded in tissue that is subsequently probed with an external magnetic field, magnetic particles that are far below saturation move along the axis on which the field B has a dominant gradient, as it follows from the force equation:

$$F_p = \frac{V_p(\chi_p - \chi_{bg})\nabla B^2}{2\mu_0},$$

where $F_p$ is the magnetic force acting on a magnetic particle with volume $V_p$ and magnetic susceptibility $X_p$, $X_{bg}$ is the magnetic susceptibility of the sample, and $\mu_0$ is the space permeability.[4] When the magnetic field at the site being probed has a dominant vertical component along which it varies (parallel or substantially parallel to the probing beam as in the sample-magnetic field configuration of the sample arm of the system shown in FIG. 3), it engages the magnetic particles in motion along this direction.

In a preferred aspect of the method of the present invention, the electromagnet current I(t) is continually modulated by an offset sinusoid at frequency $f_B$:

$$I(t) = I_{max}\sqrt{\frac{\sin(2\pi f_B t) + 1}{2}}.$$

A square-root is used to achieve a resulting magnetic gradient force (proportional to the square of the magnetic field) that is a pure sinusoid with frequency $f_B$. When a sinusoidal force at frequency $f_B$ is applied by the magnetic particles to a specific location (for example, at a depth position corresponding to $\tau_0$) in the tissue, it will respond by undergoing a displacement $$\Delta z(t) = A \sin(2\pi f_B t + \phi),$$

where A is the amplitude and $\phi$ the mechanical phase lag. The optical phase changes $\Delta\phi$ in the complex analytic signal are related to the displacements $\Delta z$ in the sample by:

$$\Delta\varphi = \frac{4\pi}{\lambda_0}\Delta z.$$

We can then write the resulting time-varying OCT signal $\tau_0$ as:

$$\tilde{S}_{OCT}(\tau_0, \Delta z) = S_{env}(\tau_0 + 2n\Delta z/c)\exp(i\phi(\tau_0) + i(4\pi n\Delta z/\lambda))$$

where n is the refractive index, c the speed of light in vacuo, and $\lambda$ the center wavelength of light.

In the "slowly varying envelope approximation", which is often a valid assumption for OCT, we can assume that the phase term in the exponential carries the bulk of the signal if the displacements are small compared to the coherence length (the envelope width is essentially the coherence length):

$$\tilde{S}_{OCT}(\tau_0, \Delta z) \approx S_{env}(\tau_0)\exp(i\phi(\tau_0) + i(4\pi n\Delta z/\lambda)) \text{ for } \Delta z << l_c/n =$$

$$\tilde{S}_{OCT}(\tau_0, 0)\exp(i(4\pi n\Delta z/\lambda))$$

where $l_c$ is the coherence length of the light.

To couple this with B-mode OCT scanning, the magnetic field is preferably modulated several cycles during the time taken to mechanically sweep the imaging light across one resolution length, which means that:

$$f_B > \frac{v_{scan}}{\Delta x},$$

where $V_{scan}$ is the transverse scan velocity, and $\Delta x$ is the transverse image resolution. In this way, the transverse Fourier transform of the spectral-domain interferogram yields a magnetomotive signal at a higher frequency than the structural OCT image data band. To produce an OCT image of tissue motion induced by the force of the magnetic field on the magnetic particles, the data $\tilde{S}_{OCT}$ is band pass filtered about $f_B$ at each depth position $\tau_0$ with a bandwidth of $v_{scan}/\Delta x$ and subsequently inverse Fourier transformed.

This works because for displacements small compared to the wavelength:

$$\exp(i(4\pi n\Delta z/\lambda)) \approx 1 + i(4\pi n\Delta z/\lambda) \text{ for } \Delta z << \lambda/n,$$

and thus $\tilde{S}_{OCT}$ is directly proportional to $\Delta z$. An advantage of this technique is that the magnetomotive signal is automatically weighted by the strength of the OCT signal (light scattering signal) at each point. This rejects large amounts of unwanted noise at pixels where there is low light intensity.

Figure 9:
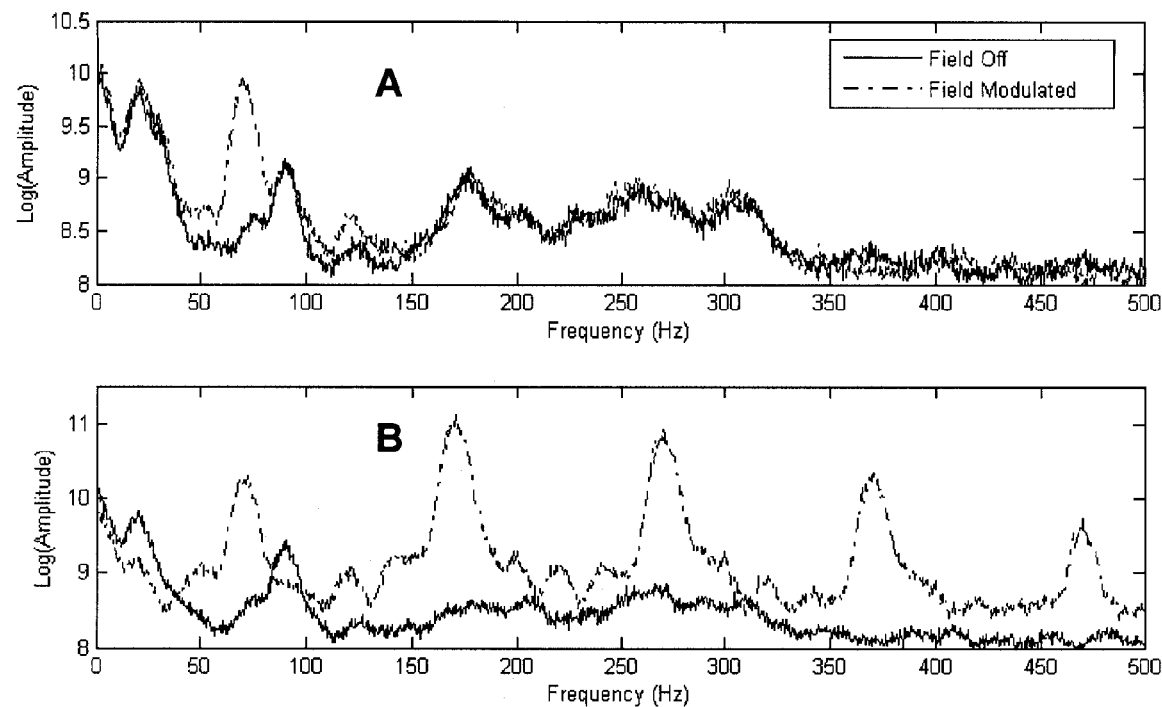
FIG. 9 shows graphs of image-averaged transverse Fourier transforms of SD-MMOCT data for tissue phantoms with 120 ppm magnetic particles (A) and 930 ppm magnetic particles (B), with $f_B$=100 Hz and a downshift of −30 Hz due to the lens.

Example transverse Fourier spectra are shown in FIG. 9. For each sample, a pair of images were acquired with and without magnetic field modulation at $f_B = 100$ Hz, which is well above $v_{scan}/\Delta x = 12.5$ Hz. In practice during transverse scanning across the imaging lens, a phase ramp is applied which downshifts the modulation signals by 30 Hz. However, this effect is predictable, and M-mode images exhibit no downshifting.

It was also found that for higher magnetic particle concentrations, harmonics of $f_B$ appear. Under these conditions the displacement $\Delta z$ is large and the approximation used above is not always valid. The signal, without any approximation, is:

$$\tilde{S}_{OCT}(\tau_0, 0)\exp(i(4\pi n\Delta z/\lambda)) = \tilde{S}_{OCT}(\tau_0, 0)\exp(i(4\pi n/\lambda)A\sin(2\pi f_B t + \phi)),$$

which is a Bessel function of the first kind exhibiting harmonics of $f_B$ for sufficiently large displacements $\Delta z$. These harmonics of $f_B$ reduce the strength of the signal at the fundamental frequency $f_B$.

Figure 10:
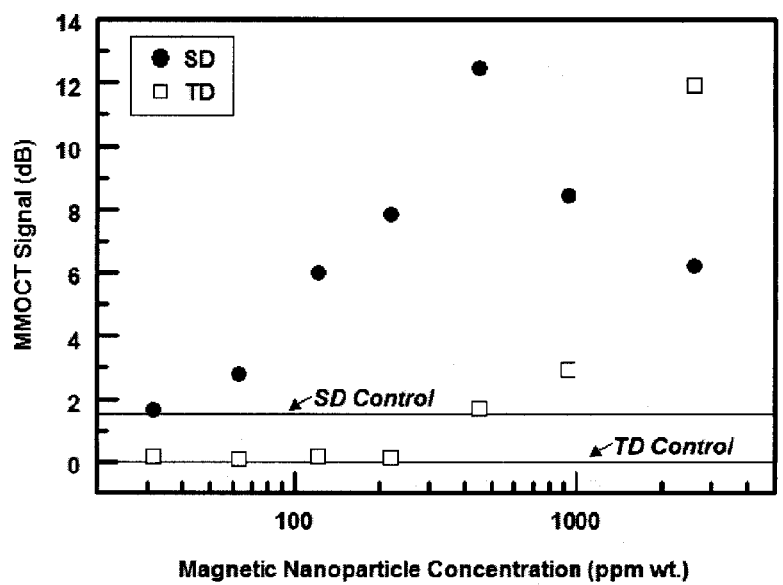
FIG. 10 is a comparison of concentration-dependent SNR (signal-to-noise ratio) for SD-and TD-MMOCT; horizontal lines indicate the SNRs of the control phantom.

Using this technique, the signal-to-noise ratio (SNR), defined as the integrated intensity at $f_B$ compared to control, is greatly improved from the previous TD-MMOCT system using the 3-pulse method.[8] The concentration-dependent SNRs are shown in FIG. 10. While TD-MMOCT affords a sensitivity to only 500 ppm magnetite particles, the SD-MMOCT system detected tissue phantoms with ~50 ppm particles. This is because the SD-MMOCT interferogram is phase-sensitive, whereas the previous TD-MMOCT data is demodulated to remove the phase contribution (because the moving delay arm decorrelates the phase between successive axial scans). The non-zero control value for the SD-MMOCT data is likely due to diamagnetic repulsion from the bulk phantom material which is made of silicone. Saturation of the SD-MMOCT SNR at higher magnetic particle concentrations occurs when the modulation signal shifts into the harmonics of $f_B$.

In an alternative aspect of the present invention, the "slowly varying envelope approximation" is not used, and the optical phase is directly processed by the full four-quadrant arctangent to pull out the phase term:

$$\phi(\tau_0, \Delta z) = \text{unwrap}(\arctan(\tilde{S}_{OCT}(\tau_0, \Delta z))) = \phi(\tau_0) + 4\pi n\Delta z/\lambda.$$

Figure 13:
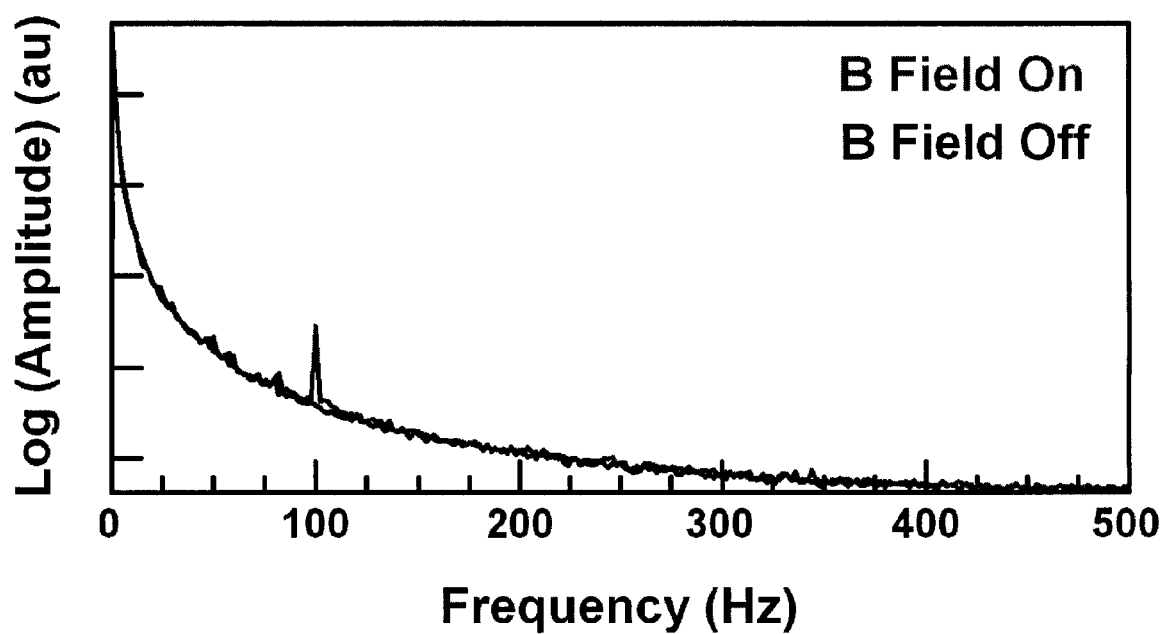
FIG. 13 shows example spectra of $\phi$ from a 100 ppm phantom.

A phase unwrapping technique[44] ("unwrap"; a one-dimension phase unwrapping technique) is preferably used in this aspect of the present invention. This no longer requires that $\Delta z$ be small compared to the wavelength, unlike when the "slowly varying envelope approximation" is used. One can then bandpass filter $\phi$ around $f_B$ at each depth position $\tau_0$. The resulting signal is the MMOCT image. Thresholding based on the amplitude of $\tilde{S}_{OCT}$ at each pixel is preferably also be performed, since this calculation does not have the advantage of the "slowly varying envelope approximation": the magnetomotive signal is not automatically weighted by the strength of the OCT signal at each point, and unwanted noise may be present at pixels where there is low light intensity. Example spectra of φ from a tissue phantom containing 100 ppm magnetic particles are shown in FIG. 13.

In another aspect of the present invention, elastography imaging is carried out using SD-MMOCT, to determine the viscosity and elastic modulus of the sample or specific parts of the sample. A sinusoidally driven visco-elastic system can be modeled by the following equation of motion:

$$z''(t) = q_0 \sin(\omega t) - \gamma z'(t) - \omega_0^2 z(t)$$

where z' and z'' are the first and second derivatives of position z with respect to time t, $q_0$ is the force per unit mass, $\omega$ is the angular driving frequency (=2 $\pi f_B$), $\gamma$ is a damping angular frequency that is proportional to the viscosity, and $\omega_0$ is the natural angular frequency of the system, where the elastic modulus is proportional to $\omega_0^2$. In the underdamped case ($\gamma < 2\omega_0$):

$$A = \frac{q_0}{\sqrt{\gamma^2 \omega^2 + (\omega_0^2 - \omega^2)^2}}$$

$$\phi = \arctan\left(\frac{\gamma \omega}{\omega_0^2 - \omega^2}\right)$$

The amplitude thus exhibits a mechanical resonance at $$\omega_{resonant} = \sqrt{\omega_0^2 - \frac{\gamma^2}{2}}$$

and the width of the resonance is proportional to $\gamma$.

By applying a chirped modulated force to the sample, $F(t)=I^2(t)$ (where I is the actual current applied to the electromagnet), the mechanical frequency spectra of $A(\omega)$ and $\phi(\omega)$ can now probed. If the system is similar to the under-damped model described above, it is then possible to determine $\gamma$ and $\omega_0$ (especially if a comparison is made with a sample of known viscosity and/or elastic modulus). This is done as follows: a chirped waveform from 0 to 2 kHz was applied to a sample consisting of 2% agarose gel embedded with magnetic particles, and imaged in M-mode. The optical phase was then directly processed by the full four-quadrant arctangent to pull out the phase term. Then the Fourier transform (FT) of the modulation force F(t) was divided from that of the unwrapped optical phase φ.

$$A(\omega) = \left|\frac{FT(\phi(t))}{FT(F(t))}\right|$$

$$\varphi(\omega) = \arctan\left(\frac{FT(\phi(t))}{FT(F(t))}\right)$$

Figure 14:
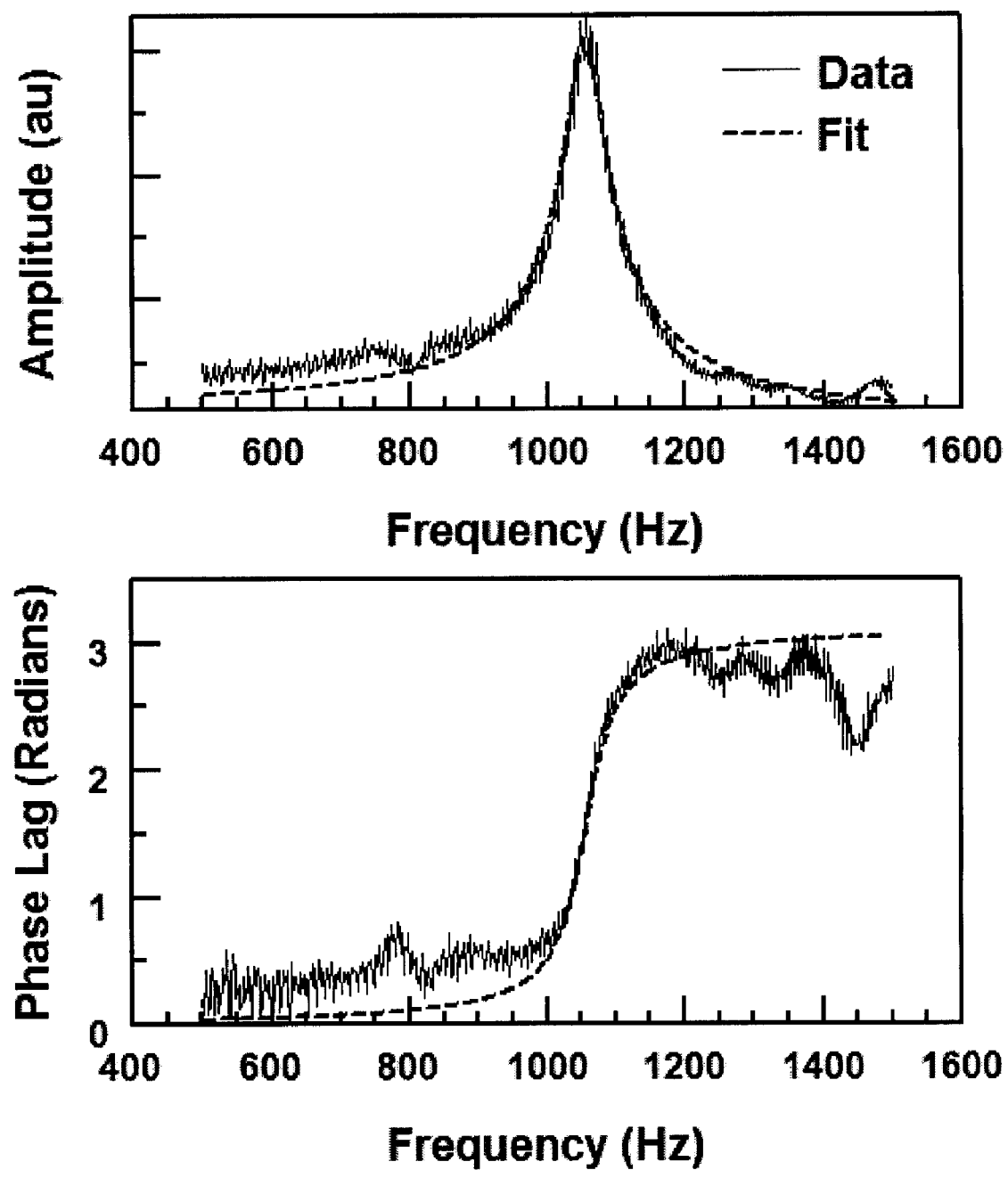
FIG. 14 shows the mechanical frequency spectra of (A) $A(\omega)$ and (B) $\phi(\omega)$, when a chirped modulated force is applied to the sample.

$A(\omega)$ was averaged over the pixels of $\tilde{S}_{OCT}$ that were significantly above the noise floor. The "phasor sum" was used to average φ over the same region. This method was applied to a 2% agarose tissue phantom containing magnetic nanoparticles. A least-squares fitting method was used to extract the frequencies $\gamma/2\pi$ and $\omega_0/2\pi$ from $A(\omega)$ in the range from 500 to 1500 Hz, and the values obtained were 67 Hz and 1058 Hz, respectively. The spectra and fit curves are plotted in FIG. 14.

This method allows one to measure the depth-dependent $\gamma$ and $\omega_0$ at a single transverse location in the sample (in M-mode). Transverse stepping can then be performed to construct a 2-or 3-D elastography image.

While the $\phi(\omega)$ was not used in the fitting in this example because it was noisy, it is a useful parameter for two reasons:

1. If it is close to zero, then the modulation response is in phase with the driver, and thus is below the resonance. If close to π, the driving frequency is above the resonance. Thus, no special fitting is needed and this simple test could be used to quickly find the general frequency range of the mechanical resonance before performing a frequency-swept scan.
2. φ can be used to differentiate between a sample that is paramagnetic or diamagnetic. A paramagnetic sample is pulled towards the magnet and thus will have an in-phase response (φ=0) at low frequencies (such as the magnetic particles themselves). A diamagnetic sample (such as the water-filled agarose itself) is diamagnetic, and will be pushed away from the magnet, resulting in φ=π. This can be used to better reject the diamagnetic response from the desired paramagnetic contrast from the magnetic particles, resulting in better imaging sensitivity.

EXAMPLES

Example 1

The SD-OCT system used in the examples includes two commercial lasers, a single-mode fiber interferometer, galvanometer mirrors for scanning the beam across the sample, a line scan CCD camera, commercial D-A and A-D converters, and computer software to control the scanning and data acquisition, and processing. In addition, for magnetic particle contrast, a water-jacketed solenoid coil which allows the laser light to pass through the central bore is positioned immediately above the sample (this electromagnet has been previously described[8]) and powered with a 1 kW power supply and controlled by the same computer, with software to synchronize the electromagnet modulation with the scanning and data acquisition.

This example demonstrates the feasibility of MMOCT in a spectral-domain OCT system (SD-MMOCT), and compares the sensitivities of amplitude and phase detection for improved imaging performance. The phase stability of the SD-OCT system was calculated as the standard deviation of the phase from a perfect reflector[10] (mirror) and was found to be 0.18 rad. In terms of physical displacement and given the bandwidth and the center wavelength of our source, this translates to approximately 11 nm displacement sensitivity. These values of sensitivity are larger than those reported for spectral-domain phase microscopy most likely because our SD-OCT system is a dual-path interferometer and thus the phase stability is vulnerable to jitter in the relative path lengths (such as those caused by temperature fluctuations and fiber bending or moving) and other noise sources that common-path systems can significantly reduce.[10-12] Compared to time-domain phase stability, however, this is an important improvement (for example, a time-domain OCT system with Fourier domain optical delay using a resonant scanning mirror exhibits a phase stability of ~1 rad at 100 Hz).

Figure 2:
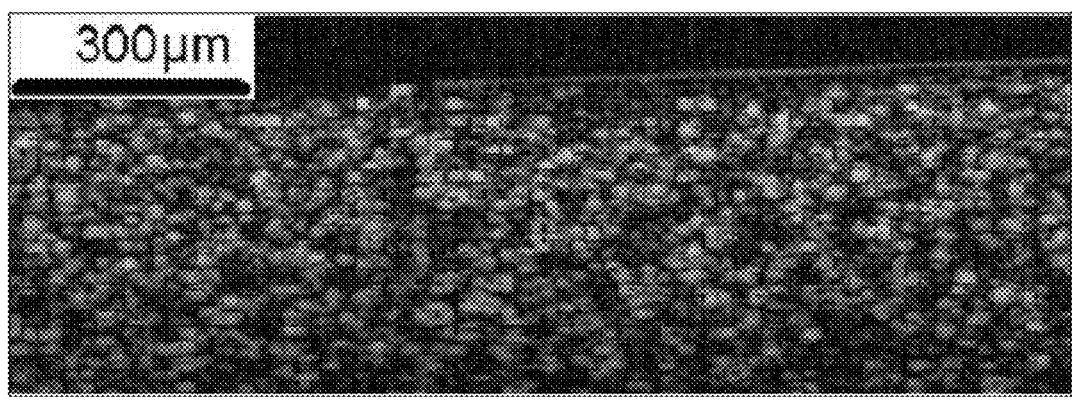
FIG. 2 is an amplitude OCT image of a tissue-like phantom showing presence of light scatterers throughout the volume.

The optical and mechanical properties of the silicone-based tissue phantoms imaged in this study match closely those of biological tissue, for example human skin.[2] Titanium dioxide ($TiO_2$) microparticles with a diameter of about one micron served as scatterers. Magnetite ($Fe_3O_4$) particles with a mean diameter between 20-30 nm were homogeneously dispersed in the sample medium for a magnetic sample (FIG. 2). A separate base stock was prepared for the control sample and no magnetic particles were added to it.

The samples were probed with 13 mW of optical power from a broadband titanium: sapphire laser (KMLabs, Inc.) centered at 800 nm and with a bandwidth of about 115 nm, providing an axial resolution of 3 µm. The magnetic field was applied by means of a computer-controlled electromagnet (FIG. 3) that was synchronized with the data acquisition and a lateral scanning mirror (the x galvanometer). The sample light was collimated through a 40 mm focal length achromatic lens and subsequently focused, providing 16 µm lateral resolution. The magnetic particle concentration of the sample used in this study of the magnetomotion was 2.5 mg/g, as the response of this sample to changes in magnetic field were evident in amplitude data and phase data.

Figure 4:
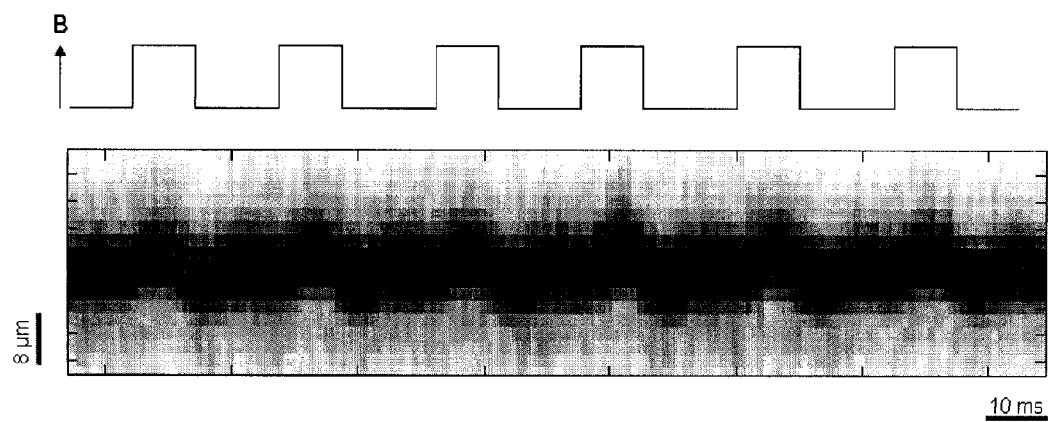
FIG. 4 is a graph of amplitude (grey-scale pixelated) and group delay (line through center of graph) data obtained using SD-MMOCT in M-mode from the top surface of a tissue-like sample containing magnetic particles, while the magnetic field is turned on and off periodically (line over graph).

In a first set of experiments, spectral domain data was acquired at a fixed position in the sample (M-mode imaging) in order to reveal the time evolution of the amplitude and phase over the depth of the sample, while the magnetic field was periodically turned on and off. Axial scans were acquired with a camera line rate of 1 kHz. The power dissipated on the electromagnet was 100 W, corresponding to a power supply control voltage of 7.5 V. The period of a cycle was about 25 ms, with a duty cycle of 32% (magnetic field modulated at 40 Hz). The results of this experiment indicate that the time scale of the sample response to magnetic field changes (either displacing when the field is turned on, or relaxing when the field is turned off), is comparable to, if not larger than, the duration of a cycle. It is difficult to assess if the agents and the sample have enough time to complete motion and reach equilibrium with the present magnetic field modulation period. Therefore, in order to better evaluate these time scales, measurements of magnetomotion with the magnetic field modulated at lower frequencies were done subsequently and are discussed below. Nonetheless, magnetomotion is evident in the data shown in FIG. 4. The fluctuations in the amplitude and in the group delay of the unwrapped phase match the magnetic field modulation, as expected. The stability of the phase allows for the unwrapping of the phase for the calculation of the group delay.[29]

Figure 5:
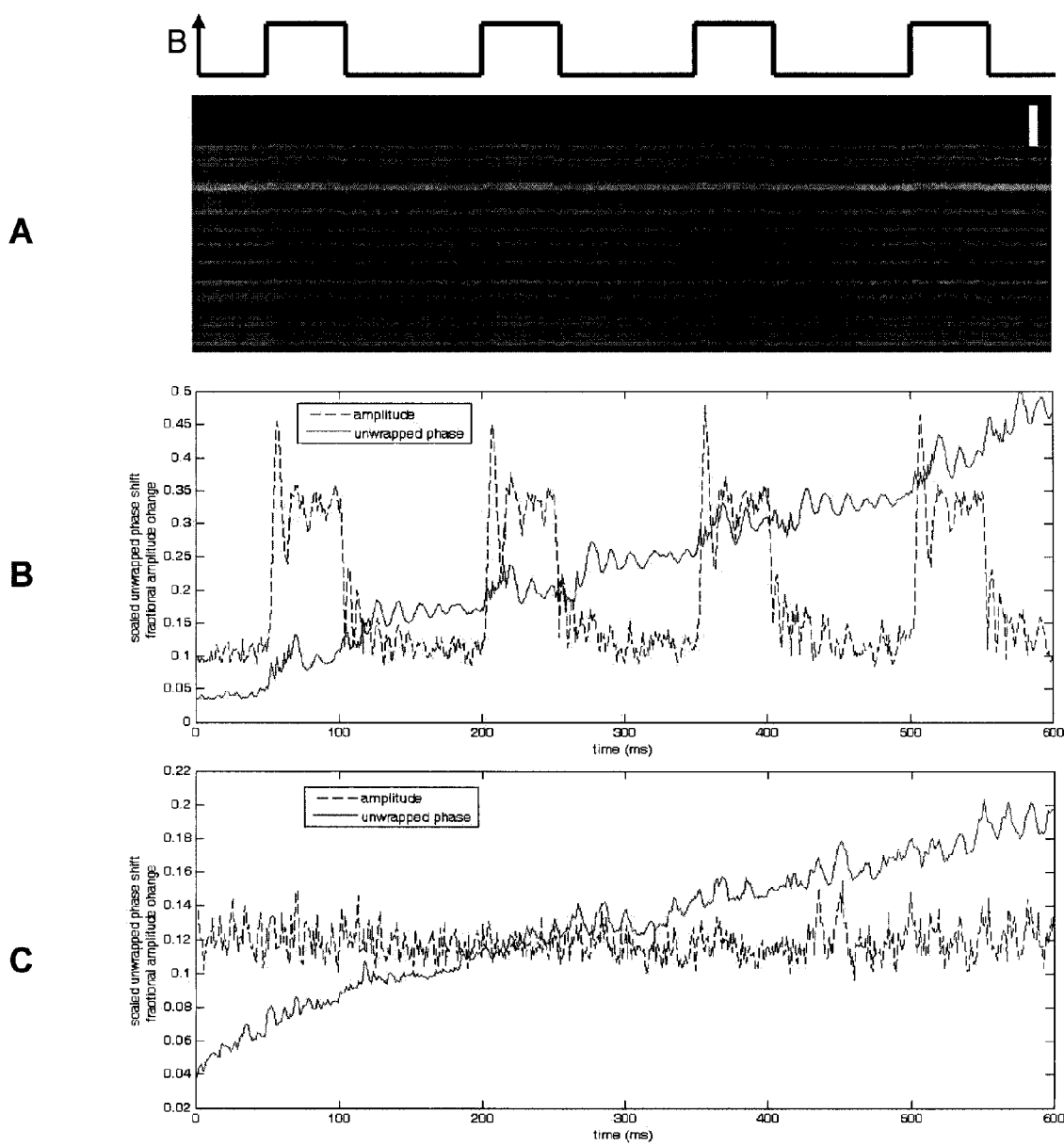
FIG. 5 shows M-mode SD-MMOCT data for a magnetic and a control sample with the magnetic field modulated at 6.67 Hz, camera line rate 1 kHz, and electromagnet control voltage of 7.5 V: (A) depth varying amplitude image (vertical scale bar=0.3 mm) for the magnetic sample; (B) a graph of fractional mean of absolute value amplitude variation and scaled mean unwrapped phase variation over all depths for the magnetic sample (according to Eqs. 1 and 2); and (C) a graph of fractional mean of absolute value amplitude variation and scaled mean unwrapped phase variation over all depths for the control sample.

Further, the magnetic field was modulated at 6.67 Hz, while the camera rate was kept at 1 kHz. The amplitude and unwrapped phase M-mode data are shown in FIG. 5. From the amplitude image alone (FIG. 5A) it might appear that at this frequency of the magnetic field the particles have enough time to reach an equilibrium position after both transitions. However, the averaged absolute value of the amplitude difference with respect to a background (zero-magnetic field) value for each row and the corresponding averaged unwrapped phase shift, defined as $$a_{frac}(t) = \frac{<|a(z,t) - <a(z,t)>_{t\_beforeBon}|>_z}{<a(z,t)>_z}, \quad \text{(Eq. 1)}$$

and $$\phi_{frac}(t) = \frac{<|\phi(z,t) - <\phi(z,t)>_{t\_beforeBon}|>_z}{<\phi(z,t)>_z}, \quad \text{(Eq. 2)}$$

and plotted in FIG. 5B, show that the scatterers appear to be exhibiting under-damped oscillations immediately after the changes in the magnetic field occur. This result constitutes the basis for dynamic studies of these oscillations. The phase modulation and the amplitude modulation, synchronized with the magnetic field modulation, are in good agreement. The analyzed data indicates that the strongest achievable MMOCT signal can be captured within a few milliseconds of the onset of the magnetic field (in this case, the mean time between onset of magnetic field and maximum displacement is 7 ms), but this will be dependent on the regional micromechanical properties of the sample or tissue. The corresponding data for the non-magnetic phantom in the presence of the magnetic field modulation is shown in FIG. 5C. As expected, the power spectra of both amplitude and phase data for this control sample do not have peak components at 6.67 Hz, since the magnetic field should not trigger a response in a non-magnetic sample. A systematic phase drift over time is apparent in both the magnetic sample and the control data, while the amplitude has a steady profile throughout an entire scan. This indicates that phase measurements should utilize correction methods for measurements over longer times.[29]

Figure 6:
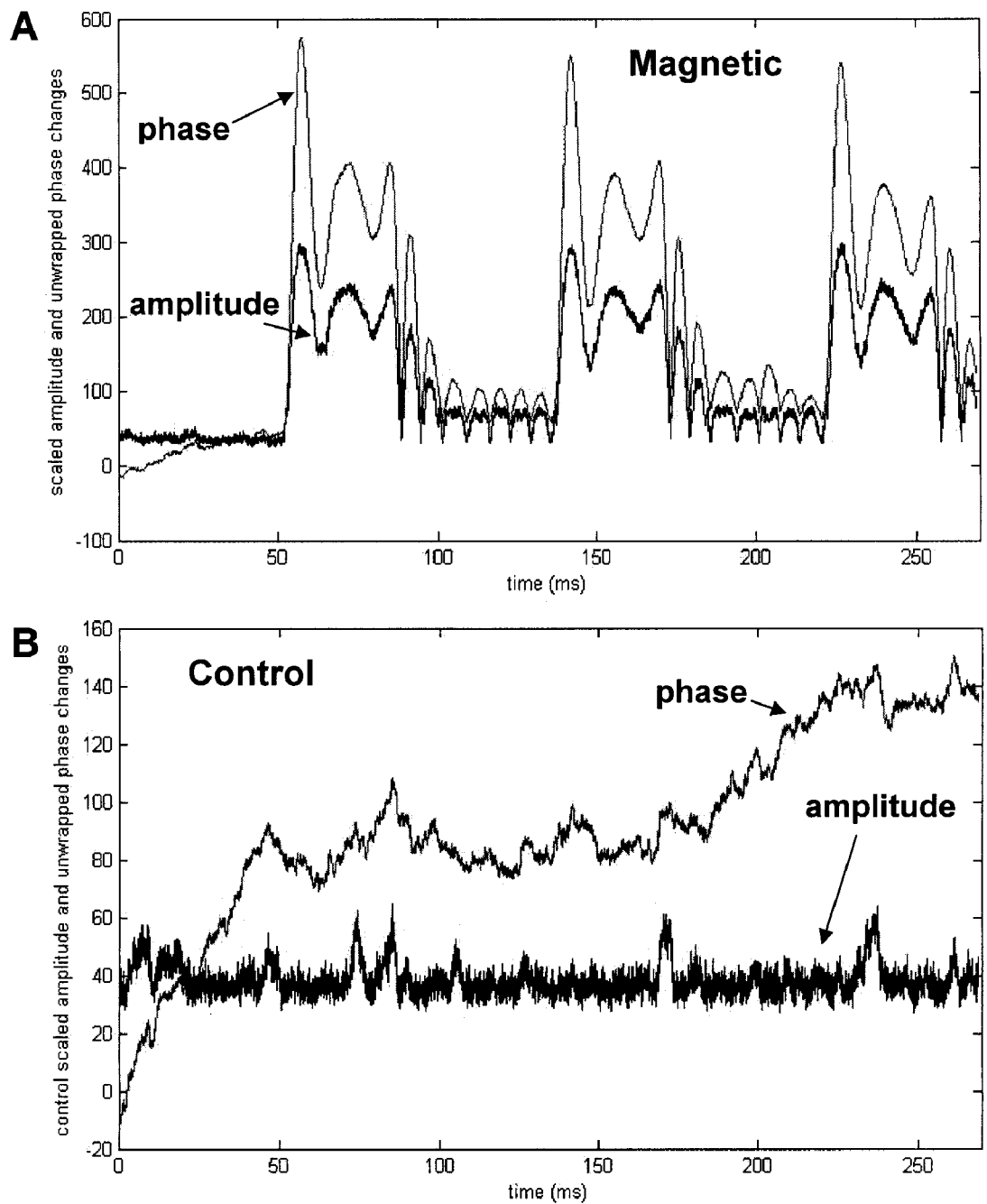
FIG. 6 shows graphs of M-mode SD-MMOCT amplitude and phase data (according to Eqs. 1 and 2) with the magnetic field modulated at 11.6 Hz, camera line rate 29 kHz, and electromagnet control voltage of 7.5 V: (A) magnetic sample; and (B) control sample.

In another experiment, the magnetic field strength was varied by changing the electromagnet power, and 8100 axial scans were acquired with a camera line rate of 29 kHz. This high frequency allows for higher sampling of the oscillations at the transitions between different states of the magnetic field. The magnetic field was modulated at 11.6 Hz in order to accommodate a set of three off-on transitions over the whole duration of a scan, which was 279.3 ms. The magnetic field strength is proportional to the power supply control voltage. The results of this experiment for a magnet control voltage of 7.5 V were in good agreement with those of FIG. 5, with the advantage of better temporal resolution, as evidenced in FIG. 6.

Figure 7:
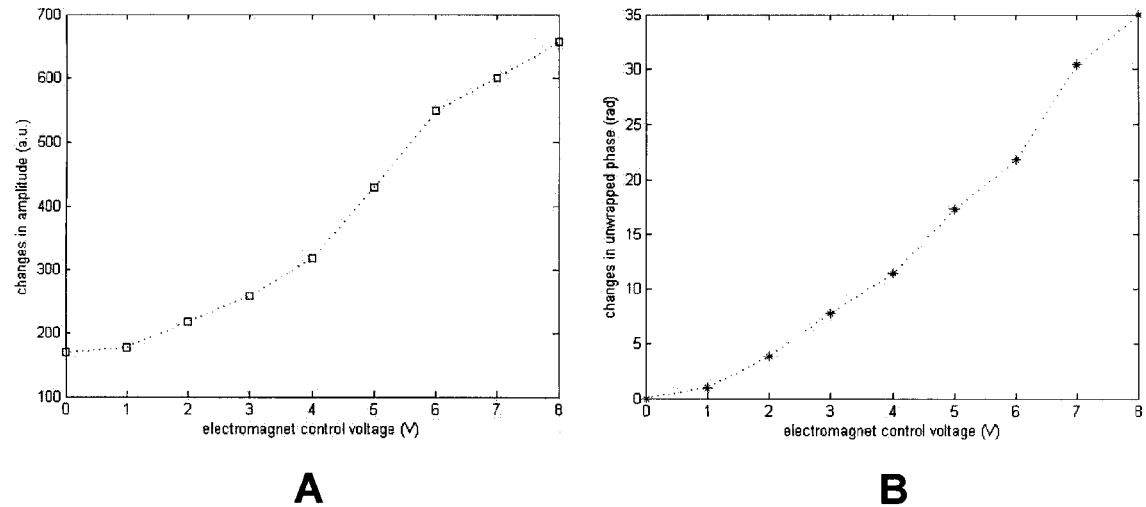
FIG. 7 shows graphs of maximum SD-MMOCT amplitude (A) and phase response (B) vs. electromagnet control voltage.

The changes in amplitude and phase as a function of electromagnet control voltage (which is linearly proportional to the magnetic field strength—for an 8V electromagnet control voltage the magnetic field strength is B=0.06 T and $\nabla B^2 \approx 1.3$ $T^2/m$) are plotted in FIG. 7. The maximum MMOCT amplitude/phase changes were calculated as the differences between the amplitude/phase values at the displacement peak immediately after the magnetic field is turned on and the mean values of amplitude/phase right before that. As expected, both amplitude and phase changes increase with the field, corresponding to an increase in the displacements in the sample.

Figure 8:
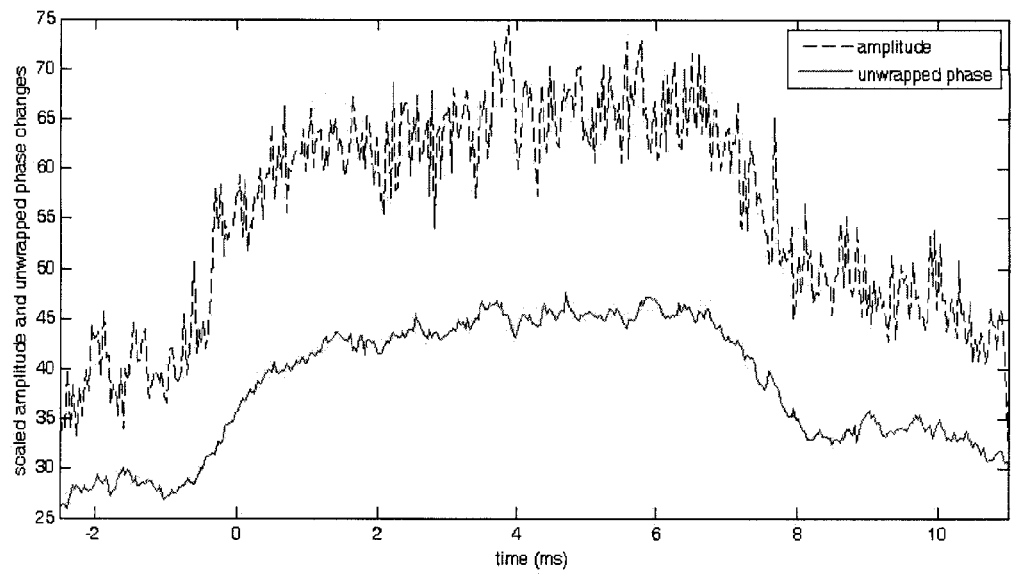
FIG. 8 shows a graph of M-mode SD-MMOCT amplitude and phase data (according to Eqs. 1 and 2) with the magnetic field modulated at 11.6 Hz, camera line rate 29 kHz, and electromagnet control voltage of 1 V.

Phase and amplitude changes for a low magnetic field corresponding to a control voltage of 1 V reveal the smallest displacement detected in this set of data. The corresponding amplitude and phase variations right before and after the magnetic field is turned on are plotted in FIG. 8. The amplitude data at this low value of the field becomes quite noisy, while the profile of the unwrapped phase is still smooth, suggesting more sensitive detection from phase analysis than from amplitude analysis. This may be close to the delineating zone between regimes in which phase versus amplitude measurements are preferred. The sensitivities for this data were calculated as the changes in amplitude and phase immediately after the field was turned on, relative to the idle state of the sample right before the field was turned on (averaging for before and after onset of field was done over ~1 ms), divided by the standard deviation of their value over the same period of non-magnetic activity. The phase signal-to-noise ratio was found to be 23.20 and the amplitude signal-to-noise ratio was 7.72, showing that in this regime phase analysis is preferable.

Example 2

Soft silicone-based tissue phantoms described previously[8] were impregnated with 4 mg/g $TiO_2$ microparticles to provide a −30/cm scattering coefficient and were added with varying concentrations of magnetite (~25 nm) particles. The OCT imaging system included an 800 nm femtosecond laser (KM-Labs) pumping a single-mode fiber interferometer with 120 nm bandwidth and ~8 mW at the sample. A 40 mm imaging lens provided 16 µm transverse resolution with axial resolution ~3 µm. The electromagnet provided ~600 G at the sample as described previously.[8] For TD-MMOCT, a delay galvanometer was modulated at 10 Hz and dual-balanced detector (New Focus Nirvana) measured the interferogram. For SD-MMOCT, a line scan camera (Dalsa) measured the spectral interferogram with an exposure time of 250 µs and line rate of 1 kHz. The image dimensions were kept at 0.5 mm wide by 0.75 mm deep for comparison, and the imaging times were 50s for TD-MMOCT and 5s (2.5s each for control and modulated images) for SD-MMOCT. The data are shown in FIGS. 9 and 10.

Example 3

Figure 11:
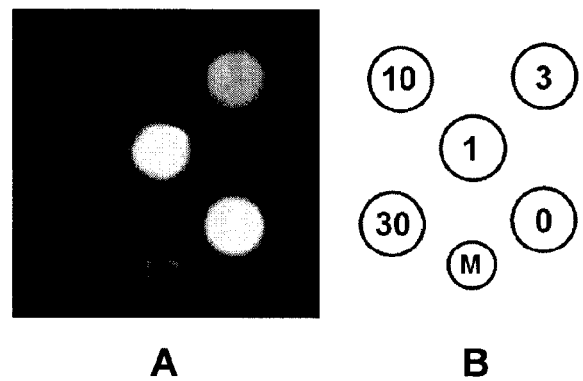
FIG. 11 is a spin-echo MRI image of agar phantoms (A) and a drawing showing the corresponding magnetic particle concentrations in the image in ppm (B); "M" is a marker.

Agar phantoms (4%) were prepared with varying concentrations of magnetite particles (Ocean Nanotech, ~10 nm) and imaged using spin-echo MRI (4.7T Varian SISCO, Trep=4s, Techo=50 ms, 10 mm slice thickness). As shown in FIG. 11, the expected negative $T_2$ contrast increases with the magnetic particle concentration, and levels <10 ppm are detectible.

Figure 12:
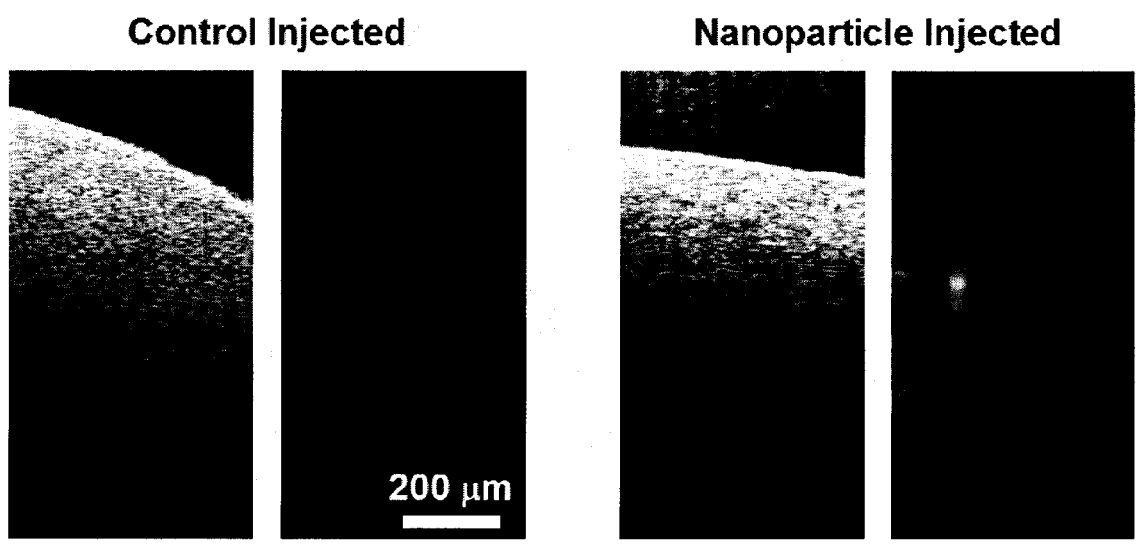
FIG. 12 shows representative structural (A and C) and corresponding magnetomotive (B and D) SD-OCT images of the spleens of control and magnetic particle injected rats, post mortem, respectively.

The same magnetic particles used in the MRI were tail-vein injected into a healthy rat (~0.5 mg/kg Fe in saline) which was euthanized after 2 hours circulation time. The major organs were harvested and compared to those from a second rat injected with a similar volume of saline only. Histology and Prussian blue staining was performed on harvested tissues, and only the spleen revealed a significant amount of magnetite particle uptake. Six sets of SD-MMOCT images (control and modulated) were then acquired from both the control and magnetic particle-laden spleens, at varying locations covering the length of the outside surface. For tissue imaging, the same SD-MMOCT parameters were used as in Example 2, except a larger depth (1 mm) was analyzed. The magnetic-specific SNR was computed for both groups, revealing an SNR of 0.095±0.29 dB for the control group. For the magnetic particle-laden spleen, four of the 6 images exhibited an SNR greater than 1 standard deviation above the control, with 0.62±0.42 dB for the group. As shown in FIG. 12, specific hot spots were observed in certain regions of the magnetic particle-laden spleen only.

REFERENCES

1. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical Coherence Tomography," *Science* 254, 1178 (1991).

2. A. F. Fercher, W. Drexler, C. K. Hitzenberger, and T. Lasser, "Optical Coherence Tomography—principles and applications," *Rep. Prog. Phys* 66 239(2003).

3. S. A. Boppart, A. L. Oldenburg, C. Xu, and D. L. Marks, "Optical probes and techniques for molecular contrast enhancement in coherence imaging," *J. Biomed. Opt.*, 10:041208 (2005).

4. A. L. Oldenburg, J. R. Gunther, and S. A. Boppart, "Imaging magnetically labeled cells with magnetomotive optical coherence tomography," *Opt. Lett.* 30, 747-749 (2005).

5. A. L. Oldenburg, J. R. Gunther, F. Jean-Jacques Toublan, D. L. Marks, K. S. Suslick, and S. A. Boppart, "Selective OCT imaging of cells using magnetically—modulated optical contrast agents," in *Proceedings of the Conference on Lasers and Electro-Optics*, pp. 405-406 (2003).

6. R. Kopelman, Y.-E. L. Koo, M. Philbert, B. A. Moffat, G. R. Reddy, P. McConville, D. E. Hall, T. L. Chenevert, M. S. Bhojani, S. M. Buck, A. Rehemtulla, and B. D. Ross, "Multifunctional nanoparticle platforms for in vivo MRI enhancement and photodynamic therapy of a rat brain cancer," *J. Magn. Magn. Mat.* 252, 404 (2005).

7. E. Romanus, M. Huckel, C. Gross, S. Prass, W, Weitschies, R. Brauer, and P. Weber, "Magnetic nanoparticle relaxation measurement as a novel tool for in vivo diagnostics," *J. Magn. Magn. Mat.* 293, 387 (2002).

8. A. L. Oldenburg, F. J. J. Toublan, K. S. Suslick, A. Wei, and S. A. Boppart, "Magnetomotive contrast for in vivo optical coherence tomography," *Opt. Express* 13, 6597-6614 (2005).

9. J. Oh, M. D. Feldman, J. Kim, C. Condit, S. Emelianov, and T. E. Milner, "Detection of magnetic nanoparticles in tissue using magneto-motive ultrasound," *Nanotechnology* 17, 4183-4190 (2006).

10. C. Joo, T. A. Akkin, B. Cense, B. H. Park, and J. F. de Boer, "Spectral-domain optical coherence phase microscopy for quantitative phase-contrast imaging," *Opt. Lett.* 30, 16 (2005).

11. M. A. Choma, A. K. Ellerbee, C. Yang, T. L. Creazzo, and J. A. Izatt, "Spectral-domain phase microscopy," *Opt Lett.* 30, 1162-1164 (2005).

12. M. A. Choma, A. K. Ellerbee, S. Yazdanfar, and J. A. Izatt, "Doppler flow imaging of cytoplasmic streaming using spectral domain phase microscopy," *J. Biomed. Opt.* 11(2), 024014 (2006).

13. M. Sticker, M. Pircher, E. Götzinger, H. Sattmann, A. F. Fercher, and C. K. Hitzenberger, "En face imaging of single cell layers by differential phase-contrast optical coherence tomography," *Opt Lett* 27, 13 (2002).

14. M. V. Sarunic, S. Weinberg, and J. A. Izaat, "Full-field swept-source phase microscopy," *Opt Lett.* 31, 10 (2006).

15. M. H. De la Torre-Ibarra, P. B. Ruiz, and J. M. Huntley, "Double-shot depth-resolved displacement field measurement using phase-contrast spectral coherence tomography," *Opt. Express* 14, 9643-9656 (2006).

16. B. J. Vakoc, S. H. Yun, J. F. de Boer, G. J. Tearney, and B. E. Bouma, "Phase-resolved optical frequency domain imaging," *Opt Express* 13, 5483-5493 (2005).

17. C. J. Pedersen, S. Yazdanfar, V. Westphal, and A. M. Rollins, "Phase-referenced Doppler optical coherence tomography in scattering media," *Opt. Lett.* 30, 16 (2005).

18. H. Ren, K. M. Brecke, Z. Ding, Y. Zhao, J. S. Nelson, and Z. Chen, "Imaging and quantifying transverse flow velocity with the Doppler bandwidth in a phase-resolved functional optical coherence tomography," *Opt. Lett.* 27, 6 (2002).

19. Y. Zhao, Z. Chen, C. Saxer, Q. Shen, S. Xiang, J. F de Boer, and J. S. Nelson, "Doppler standard deviation imaging for clinical monitoring of in vivo human skin blood flow," *Opt. Lett.* 25, 18 (2000).

20. H. Ren, Z. Ding, Y. Zhao, J. Miao, J. S. Nelson, and Z. Chen, "Phase-resolved functional optical coherence tomography: simultaneous imaging of in situ tissue structure, blood flow velocity, standard deviation, birefringence, and Stokes vectors in human skin," *Opt. Lett.* 27, 27 (2002).

21. Z. Ding, Y. Zhao, H. Ren, J. S. Nelson, and Z. Chen, "Real-time phase-resolved optical coherence tomography and optical Doppler tomography," *Opt. Express* 10, 236-244 (2002).

22. B. R. White, M. C. Pierce, N. Nassif, B. Cense, B. Hyle Park, G. J. Tearney, and B. E. Bouma, "In vivo dynamic human retinal blood flow imaging using ultra-high-speed spectral domain optical Doppler tomography," *Opt. Express* 11, 3490-3496 (2003).

23. H. Ren, T. Sun, D. J. MacDonald, M. J. Cobb, and X. Li, "Real-time in vivo blood-flow imaging by moving-scatterer-sensitive spectral-domain optical Doppler tomography," *Opt Lett.* 31, 7 (2006).

24. C. Fang-Yen, M. C. Chu, H. S. Seung, R. R. Dasari, and M. S. Feld, "Noncontact measurement of nerve displacement during action potential with a dual-beam low-coherence interferometer," *Opt. Lett.* 29, 17(2004).

25. M. A. Choma, M. V. Sarunic, C. Yang, and J. A. Izatt, "Sensitivity advantage of swept source and Fourier domain optical coherence tomography," *Opt. Express* 11, 2183-2189 (2003).

26. R. Leitgeb, C. K. Hitzenberger, and A. F. Fercher, "Performance of fourier domain vs. time domain optical coherence tomography," *Opt. Express* 11, 889-894 (2003).

27. R. A. Leitgeb, W. Drexler, A. Unterhuber, B. Hermann, T. Bajraszewski, T. Le, A. Stingl, and A. F. Fercher, "Ultrahigh resolution Fourier domain optical coherence tomography," *Opt Express* 12, 2156-2165 (2004).

28. J. F. De Boer, B. Cense, B. H. Park, M. C. Pierce, G. J. Tearney, and B. E. Bouma, "Improved signal-to-noise ratio in spectral-domain compared with time-domain optical coherence tomography," *Opt Lett.* 28, 2067-2069 (2003).

29. T. S. Ralston, D. L. Marks, P. S. Carney, and S. A. Boppart, "Phase Stability Technique for Inverse Scattering in Optical Coherence Tomography," *International Symposium on Biomedical Imaging*, 578-581 (2006).

30. C. Yang, "Molecular contrast optical coherence tomography: A review", *Photochem. Photobiol.* 81, 215 (2005).

31. J. Kim, J. Oh, T. E. Milner, J. S. Nelson, "Hemoglobin contrast in magnetomotive optical Doppler tomography," *Opt. Lett* 31, 778 (2006).

32. J. Oh, M. D. Feldman, J. Kim, H. W. Kang, P. Sanghi, T. E. Milner, "Magneto-motive detection of tissue-based macrophages by differential phase optical coherence tomography," *Lasers Surg. Med.* 39, 266 (2007).

33. V. Crecea, A. L. Oldenburg, T. S. Ralston, S. A. Boppart, "Phase-resolved spectral-domain magnetomotive optical coherence tomography," *Proc. SPIE* 6429, 64291X (2007).

34. A. L. Oldenburg, J. R. Gunther, F. J-J. Toublan, D. L. Marks, K. S. Suslick, and S. A. Boppart, "Magnetic contrast agents for optical coherence tomography," *Proc. SPIE* 5316, 91-92 (2004).

35. A. L. Oldenburg, W. Luo, S. A. Boppart, "High-resolution in vivo nanoparticle imaging using magnetomotive optical coherence tomography," *Proc. SPIE* 6097, 609702 (2006).

36. J. M. Schmitt, "OCT elastography: imaging microscopic deformation and strain of tissue," *Opt. Express* 3, 199 (1998).

37. B. Gleich, J. Weizenecker, "Tomographic imaging using the nonlinear response of magnetic particles", *Nature Letters* 435, 1214 (2005).

38. J. N. Anker and R. Kopelman, "Magnetically modulated optical nanoprobes", *Applied Physics Letters* 82 (2003).

39. Harisinghani, et al, "Noninvasive Detection of Clinically Occult Lymph-Node Metastases in Prostate Cancer," *New Engl. J. Med* 348, 2491 (2003).

40. S. Arbab, E. K. Jordan, L. B. Wilson, G. T. Yocum, B. K. Lewis, J. A. Frank, "In vivo trafficking and targeted delivery of magnetically labeled stem cells," *Human Gene Therapy* 15, 351 (2004).

41. C. Alexiou et al, "Locoregional cancer treatment with magnetic drug targeting," *Cancer Research* 60, 6641 (2000).

42. P. M. Winter, et al, "Molecular imaging of angiogenesis in early-stage atherosclerosis with integrin-targeted nanoparticles," *Circulation*, 2270 (2003).

43. S. Mornet, S. Vasseur, F. Grasset, E. Duguet, "Magnetic nanoparticle design for medical diagnosis and therapy," *J. Mater. Chem.* 14, 2161 (2004).

44. D. C. Ghiglia, M. D. Pritt, "Two-Dimensional Phase Unwrapping: Theory, Algorithms, and Software" John Wiley & Sons Inc. (1998).

45. J. Kim, J. Oh, T. E. Milner, J. S. Nelson, "Imaging nanoparticle flow using magneto-motive optical Doppler tomography," *Nanotechnology* 18, 035504 (2007).

What is claimed is:

1. A spectral-domain magnetomotive optical coherence tomography apparatus, comprising:
   (a) a spectral-domain optical coherence tomography device, and
   (b) a magnet, coupled with the optical coherence tomography device so that changes in a magnetic field are coordinated with collection of data by the optical coherence tomography device;
   wherein the magnetic field oscillates with a frequency, $$f_B > \frac{V_{scan}}{\Delta x},$$

wherein $V_{scan}$ is a transverse scan velocity of examining, and $\Delta x$ is a transverse image resolution of the examining.

2. The spectral-domain magnetomotive optical coherence tomography apparatus of claim 1, wherein the magnet is arranged so that a dominant gradient of a magnetic field produced by the magnet is aligned substantially parallel with an axial scanning direction of the spectral-domain optical coherence tomography device.

3. The spectral-domain magnetomotive optical coherence tomography apparatus of claim 1, wherein the magnet is arranged so that light from the spectral-domain optical coherence tomography device passes through the magnet during operation of the apparatus.

4. The spectral-domain magnetomotive optical coherence tomography apparatus of claim 1, further comprising (c) a computer, connected with at least one member selected from the group consisting of a magnet and an optical coherence tomography device.

5. The spectral-domain magnetomotive optical coherence tomography apparatus of claim 1, wherein the magnet is an electromagnet.

6. The spectral-domain magnetomotive optical coherence tomography apparatus of claim 1, wherein the magnet is arranged so that a dominant gradient of a magnetic field produced by the electromagnet is aligned substantially parallel with an axial scanning direction of the spectral-domain optical coherence tomography device, and light from the spectral-domain optical coherence tomography device passes through the magnet during operation of the apparatus.

7. The spectral-domain magnetomotive optical coherence tomography apparatus of claim 1, wherein the spectral-domain optical coherence tomography device comprises a broadband source.

8. The spectral-domain magnetomotive optical coherence tomography apparatus of claim 1, wherein the spectral-domain optical coherence tomography device comprises a swept source.

9. A method of examining a sample, comprising:
examining the sample with a spectral-domain optical coherence tomography device, to collect data; and
subjecting the sample to a magnetic field which is oscillating with a frequency $$f_B > \frac{v_{scan}}{\Delta x};$$

wherein the sample comprises magnetic particles, and
$V_{scan}$ is a transverse scan velocity of the examining, and $\Delta x$ is a transverse image resolution of the examining.

10. The method of claim 9, wherein the magnetic field causes the magnetic particles to move in a direction substantially parallel to a probing beam of the spectral-domain optical coherence tomography device.

11. The method of claim 9, wherein a resulting magnetic gradient force on the magnetic particles from the magnetic field is sinusoidal.

12. The method of claim 9, wherein the magnetic field is chirped.

13. The method of claim 9, wherein the magnetic field has a field modulation of 1 Hz to 10 kHz.

14. The method of claim 9, wherein the examining is B-mode scanning.

15. The method of claim 9, wherein the examining is M-mode scanning.

16. The method of claim 9, wherein phase stability of the spectral-domain optical coherence tomography device during examining is less than 0.5 rad.

17. The method of claim 9, wherein phase stability of the spectral-domain optical coherence tomography device during examining is 0.1-0.5 rad.

18. The method of claim 9, wherein the sample comprises 3 to 1000 ppm of the magnetic particles.

19. The method of claim 9, wherein the sample comprises 10 to 500 ppm of the magnetic particles.

20. The method of claim 9, wherein the sample comprises 10 to 400 ppm of the magnetic particles.

21. The method of claim 9, wherein the sample comprises 10 to 100 ppm of the magnetic particles.

22. The method of claim 9, wherein the magnetic particles comprise superparamagnetic iron oxide and/or ultrasmall superparamagnetic iron oxide.

23. The method of claim 9, wherein the magnetic particles further comprise antibodies.

24. The method of claim 9, further comprising examining the sample with magnetic resonance imaging, to collect magnetic resonance imaging data.

25. The method of claim 9, further comprising subjecting the sample to hyperthermic therapy.

26. The method of claim 9, further comprising forming an image of the sample from the data.

27. The method of claim 9, further comprising calculating an elastic modulus of the sample.

28. The method of claim 9, further comprising calculating a viscosity of the sample.

29. The method of claim 13, wherein the magnetic field has a field modulation of 1 Hz to 100 Hz.

30. The method of claim 26, wherein the image is an optical coherence tomography image, an elastic modulus image or an image of the distribution of the magnetic particles.

* * * * *